(12) United States Patent
Shimokawa et al.

(10) Patent No.: US 12,216,076 B2
(45) Date of Patent: Feb. 4, 2025

(54) VASCULAR SAP MEASUREMENT SENSOR

(71) Applicant: National University Corporation Kagawa University, Takamatsu (JP)

(72) Inventors: Fusao Shimokawa, Takamatsu (JP); Kazuma Ishida, Takamatsu (JP)

(73) Assignee: National University Corporation Kagawa University, Takamatsu (JP)

( * ) Notice: Subject to any disclaimer, the term of this patent is extended or adjusted under 35 U.S.C. 154(b) by 60 days.

(21) Appl. No.: 17/767,897

(22) PCT Filed: Oct. 8, 2020

(86) PCT No.: PCT/JP2020/038182
§ 371 (c)(1),
(2) Date: Apr. 10, 2022

(87) PCT Pub. No.: WO2021/070913
PCT Pub. Date: Apr. 15, 2021

(65) Prior Publication Data
US 2024/0085366 A1 Mar. 14, 2024

(30) Foreign Application Priority Data
Oct. 10, 2019 (JP) .................. 2019-186455

(51) Int. Cl.
*G01N 27/414* (2006.01)
*G01N 27/06* (2006.01)
(Continued)

(52) U.S. Cl.
CPC ........... *G01N 27/414* (2013.01); *G01N 27/07* (2013.01); *G01N 27/416* (2013.01); *G01N 27/06* (2013.01);
(Continued)

(58) Field of Classification Search
CPC .... G01N 27/414; G01N 27/07; G01N 27/416; G01N 27/06; G01N 2333/415;
(Continued)

(56) References Cited

U.S. PATENT DOCUMENTS 3,710,237 A * 1/1973 Watson .................. G01N 27/07
324/696
4,933,048 A 6/1990 Lauks
(Continued)

FOREIGN PATENT DOCUMENTS

DE 29604738 U1 5/1996
EP 426012 A2 * 5/1991 ............. G01N 27/07
(Continued)

OTHER PUBLICATIONS

Cranny et al., "Thick film silver-silver chloride reference electrodes", Meas. Sci. Technol. 9 (1998) 1557-1565. <https://iopscience.iop.org/article/10.1088/0957-0233/9/9/027>. (Year: 1998).*
(Continued)

*Primary Examiner* — Jonathan M Dunlap
(74) *Attorney, Agent, or Firm* — Modal PLLC

(57) ABSTRACT

A vascular sap measurement sensor includes an indicator electrode probe, a reference electrode probe, and a supporting portion. The indicator electrode probe is an ion-sensitive field effect transistor. The reference electrode probe includes a solid reference electrode, the solid reference electrode including a base layer, a silver chloride layer, and a chloride layer, the base layer being formed of an electrically conductive body, the silver chloride layer being formed on a surface of the base layer, the chloride layer being formed on a surface of the silver chloride layer. The supporting portion supports the indicator electrode probe and the reference electrode probe arranged in parallel.

10 Claims, 16 Drawing Sheets

(51) Int. Cl.
  *G01N 27/07* (2006.01)
  *G01N 27/416* (2006.01)
  *G01N 33/00* (2006.01)
  *G01R 1/067* (2006.01)
  *G01R 1/073* (2006.01)
  *G01R 27/22* (2006.01)

(52) U.S. Cl.
  CPC ... *G01N 33/0098* (2013.01); *G01N 2333/415* (2013.01); *G01R 1/06744* (2013.01); *G01R 1/06783* (2013.01); *G01R 1/0735* (2013.01); *G01R 1/07357* (2013.01); *G01R 1/07371* (2013.01); *G01R 27/22* (2013.01)

(58) Field of Classification Search
  CPC ...... G01N 33/0098; A01G 7/00; G01R 27/22; G01R 1/0735; G01R 1/06783; G01R 1/06744; G01R 1/07357; G01R 1/07371
  See application file for complete search history.

(56) References Cited

U.S. PATENT DOCUMENTS

| | | | | |
|---|---|---|---|---|
| 5,134,376 | A * | 7/1992 | Iwamoto | G01N 27/07 324/447 |
| 5,708,363 | A * | 1/1998 | Yates | G01R 27/22 324/707 |
| 6,573,734 | B2 * | 6/2003 | He | G01R 27/22 324/696 |
| 6,793,789 | B2 * | 9/2004 | Choi | G01N 27/301 204/418 |
| 9,857,391 | B2 * | 1/2018 | Shimokawa | G01N 27/04 |
| 10,948,444 | B2 * | 3/2021 | Brom-Verheyden | G01N 27/414 |
| 11,039,576 | B2 * | 6/2021 | Shimokawa | G01N 33/0098 |
| 11,143,534 | B2 * | 10/2021 | Lee | G01N 33/0098 |
| 2017/0010296 | A1 | 1/2017 | Shimokawa et al. | |
| 2019/0257681 | A1 | 8/2019 | Lee et al. | |
| 2019/0274259 | A1 | 9/2019 | Shimokawa et al. | |

FOREIGN PATENT DOCUMENTS

| | | |
|---|---|---|
| JP | S59-171852 A | 9/1984 |
| JP | H03-503677 A | 8/1991 |
| JP | H09-113478 A | 5/1997 |
| JP | 2001242134 A | 9/2001 |
| JP | 2015-145810 A | 8/2015 |
| JP | 2017-74023 A | 4/2017 |
| JP | 2019-525141 A | 9/2019 |
| WO | 2018/079186 A1 | 5/2018 |
| WO | 2019017459 A1 | 1/2019 |

OTHER PUBLICATIONS

Sophocleous et al., "An experimental analysis of Thick-Film solid-state reference electrodes," IEEE Sensors 2012. <https://ieeexplore.ieee.org/document/6411137> (Year: 2012).*

Atkinson et al., "An investigation into the effect of fabrication parameter variation on the characteristics of screen-printed thick-film silver/silver chloride reference electrodes", Microelectronics International, vol. 28, No. 2, pp. 49-52, May 10, 2011. <https://doi.org/10.1108/13565361111127368> (Year: 2011).*

Glanc-Gostkiewicz et al., "Performance of miniaturised thick-film solid state pH sensors", Sensors and Actuators A: Physical vol. 202, Nov. 1, 2013, pp. 2-7. <https://www.sciencedirect.com/science/article/pii/S0924424713001763> (Year: 2013).*

Ono et al. "Pure Photosynthates Extraction Sensor Device With Highly Precise Phloem/Xylem Position Identification", IEEE Sensors Journal, vol. 18, Iss 4, Feb. 15, 2018. <https://ieeexplore.ieee.org/document/8239793> (Year: 2018).*

Akihito Ono et al., Highly Pure Phloem-Sap-Extraction Sensor Device for Direct Component Analysis of Nutrition in Plant Shoots, Transducers 2017—19th International Conference on Solid-State Sensors, Actuators and Microsystems, 2017, pp. 1604-1607, Kaohsiung.

Akihito Ono et al., Microscale Phloem Sap Extraction Sensor Device for Measuring Biological Information in Plant Branches, IEEE Sensors, Sensors 2016—Proceedings, 2016, pp. 1-3, Orlando.

Kazuma Ishida et al., Microsensor Device for Simultaneously Measuring Moisture & Nutrient Substance Dynamics in Plants, 2019 IEEE Sensors, Oct. 27, 2019, pp. 1-4, Montreal.

Hiroki Shikata et al., New Phloem Sap Extraction and Storage Microdevice and Photosynthetic Products Analysis, 2019 IEEE Sensors, Oct. 27, 2019, pp. 1-4, Montreal.

International Search Report in International Application PCT/JP2020/038182, dated Nov. 2, 2020, pp. 1-3.

Masato Futagawa et al., "Study of a Semiconductor Type pH Sensor to Measure Low Water Content Soils in Real-time," IEEJ Transactions on Sensors and Micromachines, 2018, pp. 417-422, vol. 138, No. 9.

Kazuko Kawashima et al., "Measurement of Electrical Conductivity into Tomato Cultivation Beds using Small Insertion Type Electrical Conductivity Sensor Designed for Agriculture," IEEJ Transactions on Sensors and Micromachines, 2011, pp. 211-217, vol. 131, No. 6.

Search Report of corresponding Chinese patent application 202080069641.6, dated Feb. 22, 2024, 5 pages, CNIPA.

Chao-Lun Huang, Study of a reference electrode with dual solid resin junctions, Journal of Analytical Science, Feb. 2004, pp. 29-31, vol. 20, No. 1, China Academic Journal Electronic Publishing House, Beijing, China.

Ting Hui Ming, Electrolyte Analysis and Metrological Testing Technology, Jun. 30, 2009, pp. 127-128, China Measurement Publishing House, China.

Feng-Guang Sun et al., Design of four-electrode seawater conductivity sensor, Transducer and Microsystem Technologies, Dec. 5, 2018, pp. 86-89, 12th, China.

Search Report of corresponding Chinese patent application 202080069641.6, dated Aug. 1, 2023, 5 pages, CNIPA.

Lu Lixia, Practical Training in Chemical Engineering. Mar. 31, 2013, pp. 105-106, Beijing Institute of Technology Press, Beijing, China.

Search Report in corresponding Chinese Patent App. No. 2020800696416, Sep. 5, 2024, 4 pages, CNIPA.

* cited by examiner

VASCULAR SAP MEASUREMENT SENSOR

CROSS-REFERENCES TO RELATED APPLICATIONS

This application is the U.S. National Phase of PCT International Application No. PCT/JP2020/038182, filed on Oct. 8, 2020. That application claims priority to Japanese Patent Application No. 2019-186455, filed Oct. 10, 2019. The contents of both applications are herein incorporated by reference in their entirety.

TECHNICAL FIELD

The present invention relates to a vascular sap measurement sensor. More specifically, the present invention relates to a vascular sap measurement sensor used for measurement of, for example, a pH of vascular sap of a plant.

BACKGROUND ART

In production of crops and tree-fruits, sprinkling water and supplying nutrients at appropriate timings in accordance with growing conditions of plants are preferred from an aspect of productivity. However, in many agricultural sites, water sprinkling and supply of nutrients are performed through experience and intuition based on the number of days of no rainfall or the like at present. The method depending on the experience requires proficiency and takes a labor and time. Additionally, since indexes for criteria are based on personal experience, it is difficult for every person to easily perform the method.

Recently, a movement of introduction of information technology, such as Smart Agriculture, to agriculture becomes active. With the information technology, it is expected to perform optimal production based on biological information of plants without depending on a person.

For example, Futagawa et al., "Study of a Semiconductor Type pH Sensor to Measure Low Water Content Soils in Real-time," IEEJ transactions on sensors and micromachines, Vol. 138, No. 9, pp. 417 to 422, 2018, discloses measurement of a pH of soil. The pH of soil is used for confirmation of a state and soundness of crops. Additionally, Kawashima et al., "Measurement of Electrical Conductivity into Tomato Cultivation Beds using Small Insertion Type Electrical Conductivity Sensor Designed for Agriculture," IEEJ transactions on sensors and micromachines, Vol. 131, No. 6, pp. 211 to 217, 2011, discloses measurement of an electrical conductivity of soil. Concentrations of nutrient ingredients contained in the soil can be estimated from the electrical conductivity.

BRIEF SUMMARY

Currently, as disclosed by Futagawa et al. and Kawashima et al., generally, environments surrounding plants are monitored, for example, by measuring a pH and an electrical conductivity of soil. However, when biological information of plants can be directly measured, production of crops and tree-fruits can be further optimized.

To grow plants, a balance between water content and a nutritional substance is important. For example, in a case where the nutritional substances are too many with respect to the water content, the plant fails to take in the water content, resulting in fertilizer burn. Therefore, measuring a water dynamics of the plant is also important.

The present invention has been made in consideration of the circumstances, and one or a plurality of the following (1) to (3) is an object of the present invention.
 (1) To provide a vascular sap measurement sensor configured to directly measure a pH of vascular sap of a plant.
 (2) To provide the vascular sap measurement sensor configured to directly measure an electrical conductivity of vascular sap of the plant.
 (3) To provide the vascular sap measurement sensor configured to directly measure a dynamics of the vascular sap of the plant.

A vascular sap measurement sensor of a first aspect includes an indicator electrode probe, a reference electrode probe, and a supporting portion. The indicator electrode probe is an ion-sensitive field effect transistor. The reference electrode probe includes a solid reference electrode. The solid reference electrode includes a base layer, a silver chloride layer, and a chloride layer. The base layer is formed of an electrically conductive body. The silver chloride layer is formed on a surface of the base layer. The chloride layer is formed on a surface of the silver chloride layer. The supporting portion supports the indicator electrode probe and the reference electrode probe arranged in parallel.

In a vascular sap measurement sensor of a second aspect, which is in the first aspect, the chloride layer is produced by mixing and solidifying a glass paste and a potassium chloride at a weight ratio of 1:0.05 to 0.25.

A vascular sap measurement sensor of a third aspect, which is in the first or second aspect, includes a temperature probe that includes a temperature sensor. The temperature probe is supported by the supporting portion.

A vascular sap measurement sensor of a fourth aspect, which is in the first aspect, includes an electrical conductivity probe that includes an electrical conductivity electrode pair. The electrical conductivity electrode pair includes a pair of electrodes disposed at a predetermined interval. The electrical conductivity probe is supported by the supporting portion.

In a vascular sap measurement sensor of a fifth aspect, which is in the fourth aspect, the electrical conductivity electrode pair has a cell constant of 500 to 2,000 m$^{-1}$.

In a vascular sap measurement sensor of a sixth aspect, which is in the fourth or fifth aspect, each of the pair of electrodes includes a metal layer that covers a projection formed on a probe surface.

In a vascular sap measurement sensor of a seventh aspect, which is in any of the fourth to sixth aspects, the pair of electrodes are arranged side by side along a width direction of the electrical conductivity probe.

In a vascular sap measurement sensor of an eighth aspect, which is in any of the fourth to sixth aspects, the pair of electrodes are arranged side by side along an axial direction of the electrical conductivity probe.

A vascular sap measurement sensor of a ninth aspect, which is in any of the fourth to eighth aspects, includes a temperature probe that includes a temperature sensor. The temperature probe is supported by the supporting portion.

In a vascular sap measurement sensor of a tenth aspect, which is in the fourth aspect, the indicator electrode, the solid reference electrode, and the electrical conductivity electrode pair are disposed at a same position in a sticking direction to a plant.

In a vascular sap measurement sensor of an eleventh aspect, which is in the fourth aspect, the indicator electrode and the solid reference electrode are disposed at positions different from the electrical conductivity electrode pair in a sticking direction to a plant. The electrical conductivity electrode pair is disposed in a xylem of the plant with the indicator electrode and the solid reference electrode disposed in a phloem of the plant.

A vascular sap measurement sensor of a twelfth aspect, which is in the first or fourth aspect, includes a heater-equipped temperature probe and a temperature probe. The heater-equipped temperature probe includes a temperature sensor and a heater. The temperature probe includes a temperature sensor. The heater-equipped temperature probe and the temperature probe are supported by the supporting portion.

A vascular sap measurement sensor of a thirteenth aspect, which is in the twelfth aspect, includes two of the temperature probes. The two temperature probes are disposed at positions across the heater-equipped temperature probe.

According to the first aspect, by sticking the indicator electrode probe and the reference electrode probe to the plant, a pH of a vascular sap of the plant can be measured.

According to the second aspect, by mixing the glass paste and the potassium chloride at the weight ratio of 1:0.05 to 0.25, the chloride layer that has good adhesiveness and in which the glass paste is less likely to be dissolved can be obtained.

According to the third aspect, temperature compensation of a pH measurement value based on a temperature of the vascular sap measured by the temperature probe allows accurately measuring the pH of the vascular sap.

According to the fourth aspect, by sticking the electrical conductivity probe to the plant, an electrical conductivity of the vascular sap of the plant can be measured.

According to the fifth aspect, since the cell constant of the electrical conductivity electrode pair is 500 to 2,000 $m^{-1}$, the electrical conductivity of the vascular sap can be accurately measured.

According to the sixth aspect, configuring the electrode in a three-dimensional shape allows widening an electrode surface area. Accordingly, while the electrical conductivity electrode pair has a size such that the electrical conductivity electrode pair can be inserted into the plant, the cell constant can be decreased.

According to the seventh aspect, the pair of electrodes are arranged side by side along the width direction of the electrical conductivity probe. Accordingly, a resistance when the electrical conductivity probe is sticked to the plant can be comparatively decreased.

According to the eighth aspect, the pair of electrodes are arranged side by side along the axial direction of the electrical conductivity probe. Therefore, when the electrical conductivity probe is sticked to the plant, a clearance between the pair of electrodes runs along a vascular bundle, and the vascular sap easily passes through.

According to the ninth aspect, based on a temperature of the vascular sap measured by the temperature probe, temperature compensation is performed on an electrical conductivity measurement value. This allows accurately measuring the electrical conductivity of vascular sap.

According to the tenth aspect, since the indicator electrode, the solid reference electrode, and the electrical conductivity electrode pair are disposed at the same position in the sticking direction to the plant, the pH and the electrical conductivity of the phloem sap or the xylem sap of the plant can be simultaneously measured.

According to the eleventh aspect, the indicator electrode and the reference electrode are disposed in the phloem and the electrical conductivity electrode pair is disposed in the xylem. Thus, the electrical conductivity of xylem sap can be measured while measuring the pH of phloem sap.

According to the twelfth aspect, a flow rate of the vascular sap can be obtained from measurement values of the heater-equipped temperature probe and the temperature sensor disposed on the temperature probe.

According to the thirteenth aspect, comparison of the temperatures measured by the two temperature probes allows identifying a flowing direction of the vascular sap.

DETAILED DESCRIPTION OF EMBODIMENTS

Next, embodiments of the present invention will be described based on the drawings.

First Embodiment

A vascular sap measurement sensor 1 according to the first embodiment of the present invention can be mounted to a fine point of a plant, such as a distal end of a new branch and a pedicel of a plant. The vascular sap measurement sensor 1 has a function of measuring a pH of vascular sap at a fine point of a plant.

(Vascular Sap Measurement Sensor)

First, a configuration of the vascular sap measurement sensor 1 will be described.

Figure 1:
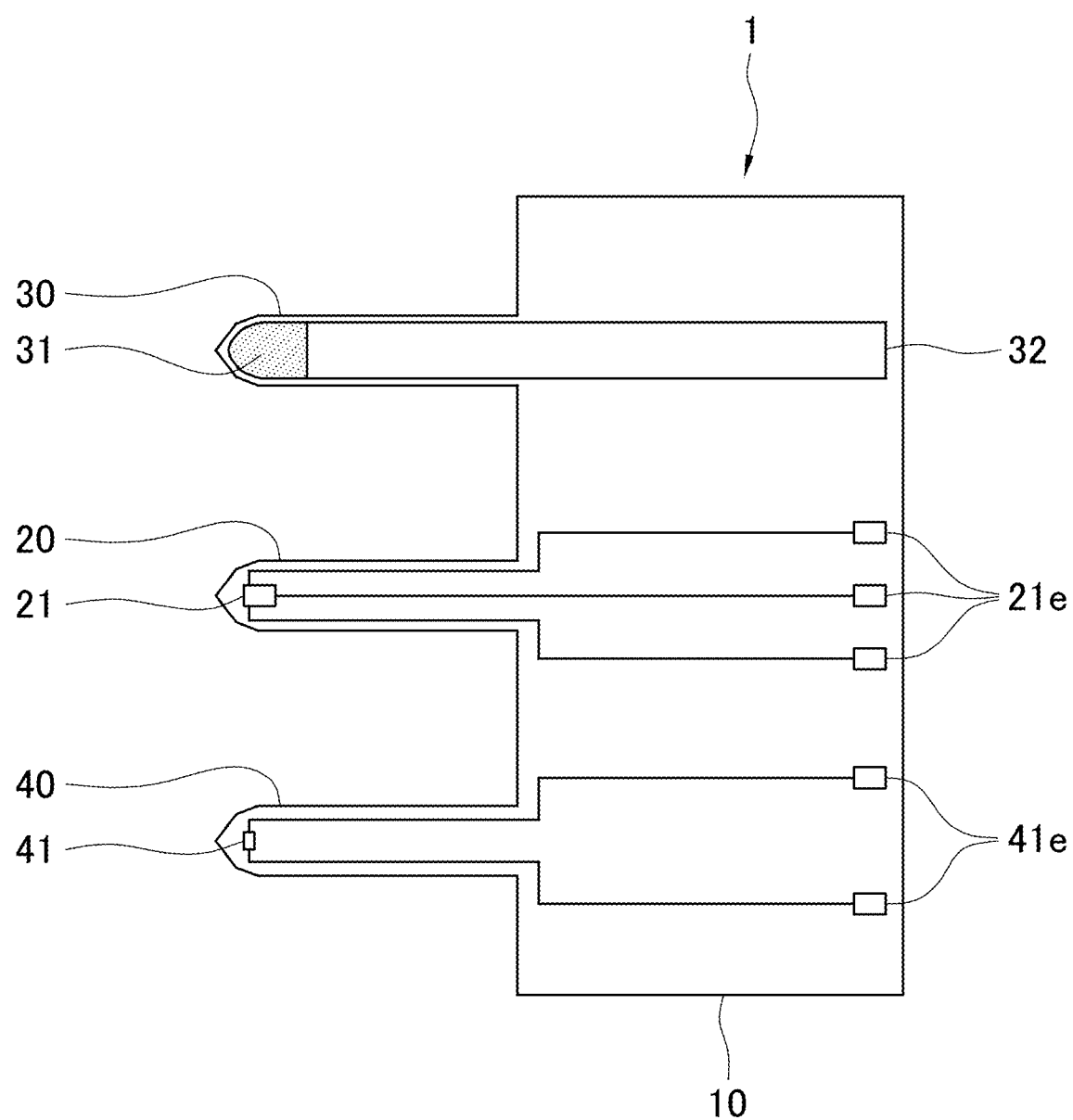
FIG. 1 is a plan view of a vascular sap measurement sensor according to a first embodiment.

As illustrated in FIG. 1, the vascular sap measurement sensor 1 includes a supporting portion 10. The supporting portion 10 is provided with an indicator electrode probe 20, a reference electrode probe 30, and a temperature probe 40. The indicator electrode probe 20 and the reference electrode probe 30 are paired to be used for pH measurement of vascular sap. The temperature probe 40 is used for temperature measurement of the vascular sap. The temperature of the vascular sap is used for temperature compensation of the pH measurement value. Accordingly, for example, when temperature compensation is unnecessary, the vascular sap measurement sensor 1 need not include the temperature probe 40.

The probes 20, 30, and 40 are arranged in parallel in the same plane, and the base ends of the probes 20, 30, and 40 are supported by the supporting portion 10. The order of arrangement of the probes 20, 30, and 40 is not specifically limited. By sticking these probes 20, 30, and 40 to the plant, the vascular sap measurement sensor 1 is installed to the plant.

The supporting portion 10 and the probes 20, 30, and 40 are formed by processing a semiconductor substrate. Examples of the semiconductor substrate include a silicon substrate and a Silicon on Insulator (SOI) substrate. As the processing of the semiconductor substrate, in addition to photolithography and etching, a MEMS technique using thin film formation, such as sputtering method and evaporation method, is used.

Supporting Portion

The supporting portion 10 is a member supporting the probes 20, 30, and 40. The supporting portion 10 is a plate material having a rectangular shape in plan view and all of the probes 20, 30, and 40 are supported by the long side portion at one side. The supporting portion 10 only needs to have a length in a longitudinal direction such that all of the probes 20, 30, and 40 can be disposed at predetermined intervals. A length in the short side direction of the supporting portion 10 is not specifically limited.

Probe

Each of the probes 20, 30, and 40 is a rod-shaped member and is disposed in a cantilever manner to the edge (the long side portion) of the supporting portion 10. The tip portion of each of the probes 20, 30, and 40 is preferably formed in a pointed shape, such as a triangular shape. The pointed tip portions of the probes 20, 30, and 40 allow decreasing an insertion resistance when the probes 20, 30, and 40 are inserted into the fine point of the plant. This allows the probes 20, 30, and 40 to be smoothly sticked to the fine point of the plant, such as a stem. This also allows reducing damage of the tip portion of the probe 20, 30, or 40 when the probe 20, 30, or 40 is sticked to the fine point of the plant.

Each of the probes 20, 30, and 40 is formed to have dimensions such that each of the probes 20, 30, and 40 can be disposed by being sticked to the fine point of the plant having a stem diameter or an axis diameter of around several mm, such as a distal end of a new branch and a pedicel of the plant. The length of each of the probes 20, 30, and 40 (the length from the base end to the tip in the axial direction) is formed to have a dimension such that the tip portion can be disposed in a xylem or a phloem of the fine point of the plant when each of the probes 20, 30, and 40 is sticked and installed to the fine point of the plant. For example, each of the probes 20, 30, and 40 has the length from 50 to 1,000 μm.

A width of each of the probes 20, 30, and 40 is not specifically limited, but is, for example, from 50 to 300 μm. The shorter the width of the probe 20, 30, or 40 is, the smaller the damage (injury) given to the plant can be.

Figure 2:
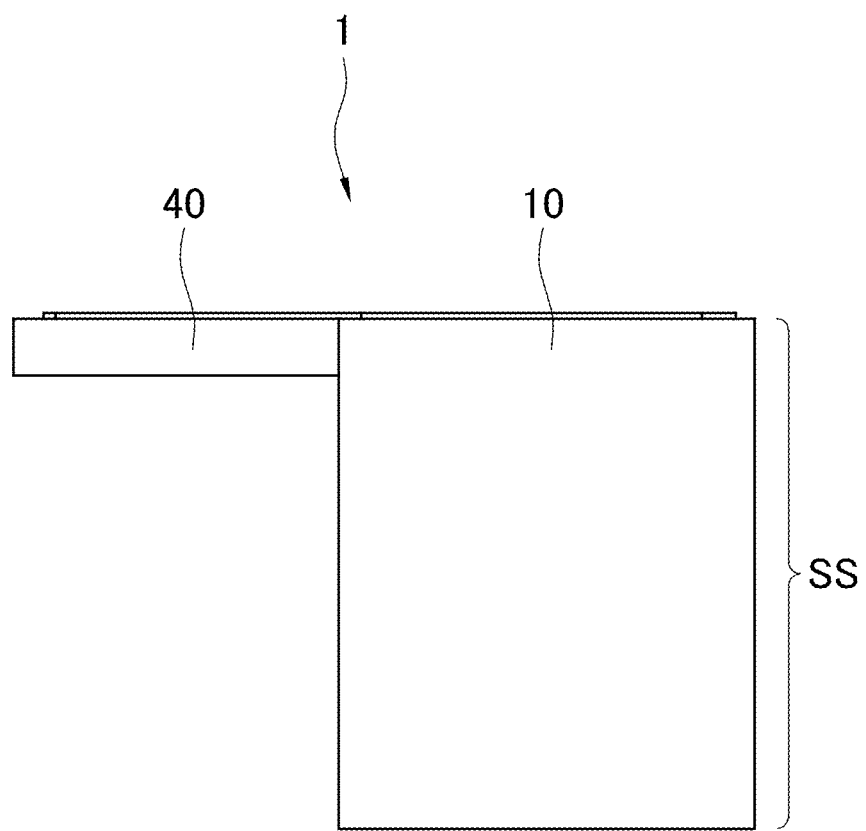
FIG. 2 is a side view of the vascular sap measurement sensor according to the first embodiment.

As illustrated in FIG. 2, each of the probes 20, 30, and 40 is formed to be thinner than the thickness of the supporting portion 10 by removing a lower portion of a semiconductor substrate SS. Each of the probes 20, 30, and 40 has the thickness configured to be shorter than the widths of the phloem and the xylem of the plant as the measurement target. Although the thickness of each of the probes 20, 30, and 40 depends on the kind and the thickness of the stem of the plant as the measurement target, the thickness is, for example, from 50 to 300 μm. The thickness of 50 μm or more provides sufficient strength, and the probe 20, 30, or 40 is free from a risk of being bent when the probe 20, 30, or 40 is inserted into and removed from, for example, the stem. Additionally, although depending on the kind of the plant, the thicknesses of the xylem and the phloem are around 100 to 400 μm, and therefore as long as the thickness is 300 μm or less, even when the probe 20, 30, or 40 is sticked to the xylem or the phloem, blocking the xylem or the phloem can be inhibited.

The probes 20, 30, and 40 having such a shape is formed in, for example, the following procedure. Photolithography of a probe shape is performed on the semiconductor substrate SS and an unnecessary part is removed by dry etching, such as ICP-RIE, to form an original shape of the probe shape. Next, the semiconductor substrate SS is etched from the back surface such that the probes 20, 30, and 40 are cantilevered. This process uses dry etching, such as ICP-RIE. The semiconductor substrate SS is etched from the back surface and the etching is terminated at a phase where the probes 20, 30, and 40 are separated. Accordingly, the probes 20, 30, and 40 in the cantilever manner can be formed.

Indicator Electrode Probe

As illustrated in FIG. 1, an indicator electrode 21 is disposed on the tip portion of the indicator electrode probe 20. The indicator electrode 21 is formed of an ion-sensitive field effect transistor (ISFET). The ion-sensitive field effect transistor does not include a metal electrode portion on a gate oxide film of a usual field effect transistor (FET), but includes an ion sensitive membrane, such as a dielectric substance, instead.

Three electrode pads 21e coupled to the indicator electrode 21 via wirings are disposed on the top surface of the supporting portion 10. The three respective electrode pads 21e are coupled to a gate electrode, a source electrode, and a drain electrode of the ion-sensitive field effect transistor.

The ion-sensitive field effect transistor is formed in, for example, the following procedure. Embedded layers (n⁺) of the source and the drain are formed on the semiconductor substrate by, for example, a diffusion process. Next, metal electrodes coupled to these embedded layers are formed by, for example, sputtering method and evaporation method. Next, ion sensitive membranes (gate oxide films) formed of a dielectric film, such as $SiO_2$ and $TaO_x$, are formed on the upper portions of them by, for example, sputtering method. Additionally, the electrode pads 21e and the wirings are formed by, for example, depositing an Al thin film on the semiconductor substrate by, for example, sputtering method and evaporation method.

Reference Electrode Probe

Figure 3:
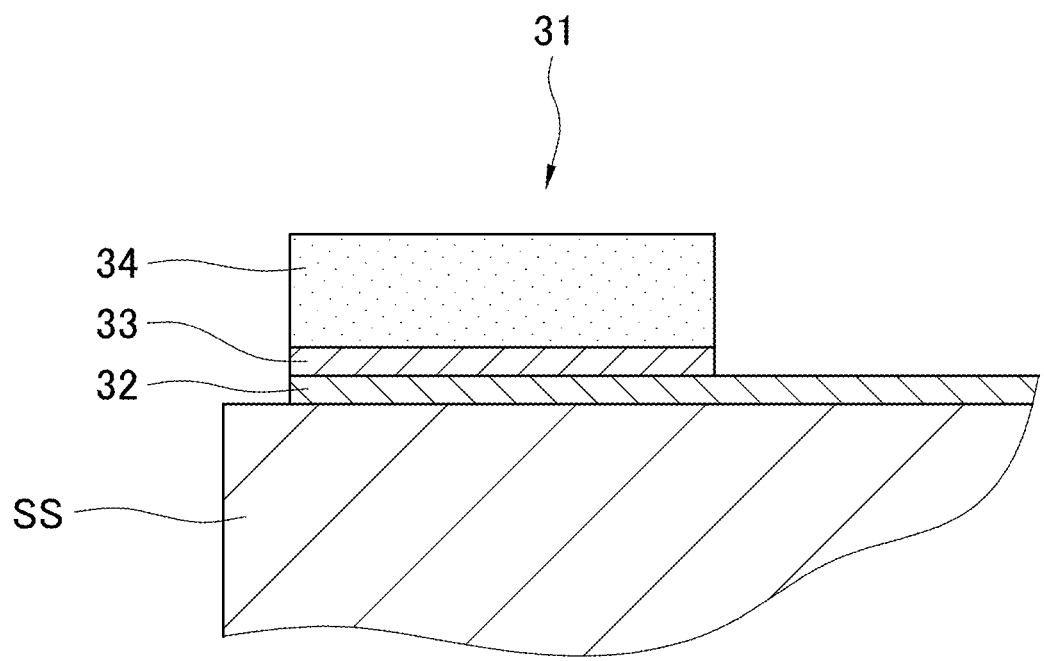
FIG. 3 is a vertical cross-sectional view of a solid reference electrode.

A solid reference electrode 31 is disposed on the tip portion of the reference electrode probe 30. The solid reference electrode 31 has a configuration illustrated in FIG. 3. That is, the solid reference electrode 31 has the configuration in which a base layer 32, a silver chloride layer 33, and a chloride layer 34 are stacked in this order. Note that the base layer 32 is extended up to the supporting portion 10 to also constitute a wiring for reading the solid reference electrode 31 (see FIG. 1).

The base layer 32 is a thin film formed of an electrically conductive body and is formed on the surface of the semiconductor substrate SS constituting the reference electrode probe 30. As the material of the base layer 32, a metal, such as Au and Al, are preferably used. The base layer 32 is formed by, for example, depositing a metal thin film on the semiconductor substrate SS by, for example, sputtering method and evaporation method.

The silver chloride layer 33 is an AgCl thin film formed on the surface of the base layer 32. The silver chloride layer 33 is, for example, formed by applying silver chloride ink over the surface of the base layer 32 and drying it. The silver chloride ink is produced by dispersing microparticles of the silver chloride crystal into a solvent.

The chloride layer 34 is formed on the surface of the silver chloride layer 33. The chloride layer 34 is a layer formed by solidifying chloride with a solidification material. For example, a potassium chloride and a sodium chloride can be used as the chloride. The solidification material only need to be a material that is chemically stable, has a neutral pH, is a porous body in the solidified state, and has an electrical insulating property. Examples of the solidification material include a glass paste, a porous material of ceramic, a high-polymer material, such as polyimide, and a madreporite material of nanocomposite made of polyimide and silica.

When the potassium chloride is used as the chloride and the glass paste is used as the solidification material, the chloride layer 34 can be formed by mixing and solidifying potassium chloride powder and the glass paste. The glass paste is a mixture of glass powder and a vehicle. The potassium chloride powder and the glass paste are mixed at a predetermined ratio, and after the mixture is applied over the surface of the silver chloride layer 33, the mixture is fired to form the chloride layer 34.

Here, in a weight ratio between the potassium chloride and the glass paste, the potassium chloride is preferably set to be 0.05 to 0.25 to the glass paste of 1. Mixing the glass paste and the potassium chloride at the weight ratio of 1:0.05 to 0.25 allows obtaining the chloride layer 34 that features good adhesiveness and in which the glass paste is less likely to be dissolved. Additionally, in the weight ratio between the potassium chloride and the glass paste, the potassium chloride is more preferably set to be 0.05 to 0.10 to the glass paste of 1. This stabilizes an output potential of the solid reference electrode 31.

Temperature Probe

As illustrated in FIG. 1, a temperature sensor 41 is disposed on the tip portion of the temperature probe 40. As long as the temperature sensor 41 has a function of sensing a temperature and a size such that the temperature sensor 41 can be disposed on the tip portion of the temperature probe 40, the temperature sensor 41 is not specifically limited. As the temperature sensor 41, a pn junction diode, a thermocouple, a resistance temperature detector, and the like can be used. On the top surface of the supporting portion 10, two electrode pads 41e coupled to the temperature sensor 41 via wiring are disposed.

The pn junction diode can be formed on the semiconductor substrate using an oxidation diffusion furnace. Specifically, after a diffusion hole (a p-type) is formed on the semiconductor substrate, n diffusion (an n-type) is formed. Next, a contact of the pn junction diode is formed, and the electrode pads 41e and the wirings are formed. Specifically, depositing the Al thin film on the semiconductor substrate by sputtering method, evaporation method, and the like forms the contact, the electrode pads 41e, and the wirings. Additionally, the thermocouple and the resistance temperature detector can be formed on the semiconductor substrate by thin film technique.

In the case of using the pn junction diode as the temperature sensor 41, the temperature is measured in the following procedure. It is known that a forward characteristic of the diode changes by temperature, and flowing a constant current through the diode changes a voltage in association with a temperature change. A constant current source is coupled between the two electrode pads 41e and 41e. The constant current is supplied to the temperature sensor 41 as the pn junction diode in a forward direction by the constant current source, and a voltage between an anode and a cathode of the temperature sensor 41 is measured by voltmeter. The temperature can be calculated from the voltage measured by the voltmeter.

(Measuring Method)

Next, the measuring method of the pH of vascular sap by the vascular sap measurement sensor 1 will be described.

Mounting

Figure 4:
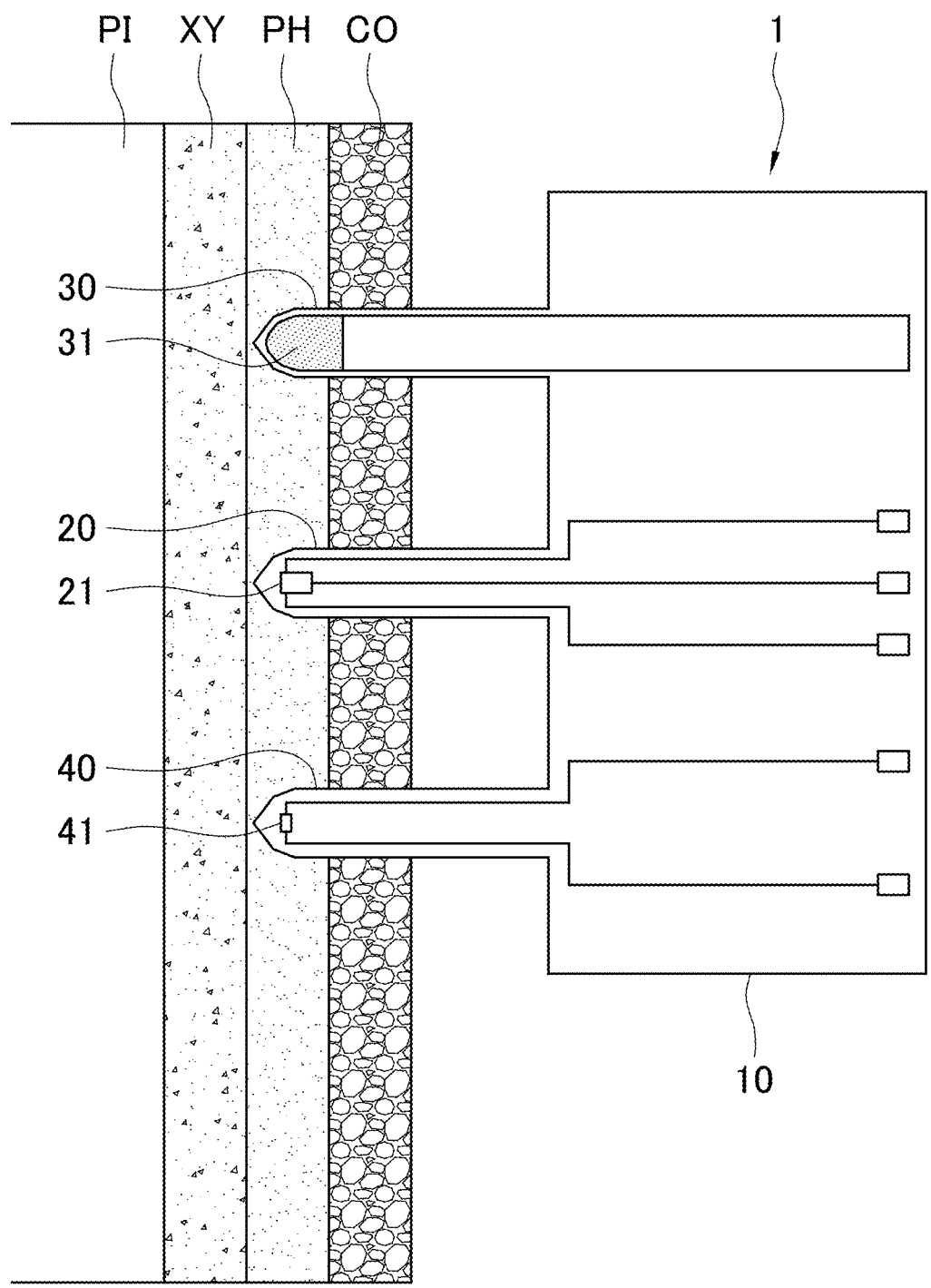
FIG. 4 is a use state explanatory view of the vascular sap measurement sensor according to the first embodiment.

First, the vascular sap measurement sensor 1 is mounted to a distal end of a new branch, a pedicel, and the like of the plant as the measurement targets. Specifically, as illustrated in FIG. 4, all of the probes 20, 30, and 40 of the vascular sap measurement sensor 1 are sticked and mounted to the plant. At this time, the probes 20, 30, and 40 are disposed along a xylem XY and a phloem PH of the plant.

When the probes 20, 30, and 40 are sticked to the plant, the tip portions of the probes 20, 30, and 40 pass through a skin layer CO of the plant to reach the phloem PH. Furthermore, when the probes 20, 30, and 40 are sticked deeply, the tip portions of the probes 20, 30, and 40 reach the xylem XY and then reach a pith PI. To measure pH of phloem sap, the tip portions of the probes 20, 30, and 40 are disposed in the phloem PH. To measure pH of xylem sap, the tip portions of the probes 20, 30, and 40 are disposed in the xylem XY.

pH Measurement

As illustrated in FIG. 4, when the tip portions of the indicator electrode probe 20 and the reference electrode probe 30 are disposed in the phloem PH, the indicator electrode 21 and the solid reference electrode 31 contact the common phloem sap.

Figure 5:
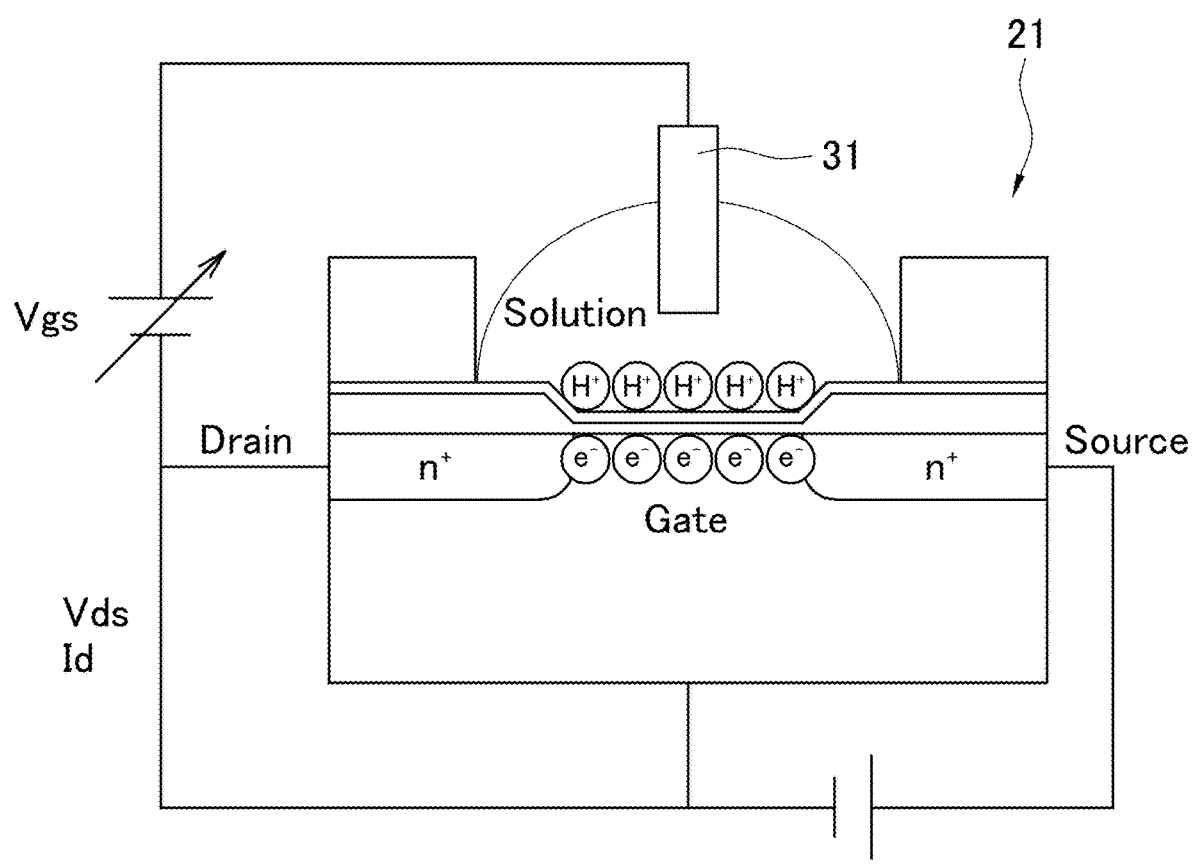
FIG. 5 is a schematic diagram illustrating a pH measurement principle.

FIG. 5 schematically illustrates a pH measurement principle. The ISFET as the indicator electrode 21 has a structure alike a MOSFET. The ISFET has a structure in which a gate electrode of the MOSFET is replaced by the ion sensitive membrane, and a gate bias is applied via a solution. A resistance between the $n^+$ type-the $p^+$ type-the $n^+$ type of silicon (Si) is 7.0 MΩ, which is considerably high, and usually only a trace current flows. A contact of the solution with the gate part positively charges the ion sensitive membrane with hydrogen ions ($H^+$) in the solution. Since the charged ion sensitive membrane attracts electrons ($e^-$) inside the silicon to the proximity of the gate by an electrical double layer, an interface potential occurs. The interface potential changes by ion concentration of the solution. Therefore, when the interface potential is detected as a Vth shift of drain current-gate voltage characteristics (Id-Vgs characteristics), the ion concentration can be measured.

Temperature Compensation

It has been known that the measurement value of pH obtained by the ion-sensitive field effect transistor depends on the temperature. This is because an electromotive force per pH changes due to the temperature of the solution. Therefore, performing the temperature compensation on the pH measurement value is preferred. Disposing the tip portion of the temperature probe 40 in the phloem PH brings the temperature sensor 41 into contact with the phloem sap. Therefore, the temperature sensor 41 can measure the temperature of the phloem sap. The temperature compensation is performed on the pH measurement value based on the temperature of the phloem sap measured by the temperature probe 40. Thus, the pH of phloem sap can be accurately measured.

As described above, the vascular sap measurement sensor 1 can measure the pH of phloem sap. The phloem sap contains a nutritional substance, such as sucrose, generated by photosynthesis. Measuring the pH of phloem sap allows quantifying the nutritional substance contained in the phloem sap. This allows grasping a health condition of the plant.

Note that disposing the tip portions of the probes 20, 30, and 40 in the xylem XY allows measuring the pH of xylem sap. Since the phloem sap contains a photosynthesis product, such as sucrose, the pH is higher than that of the xylem sap. Specifically, generally, while the pH of xylem sap is about 6, the pH of phloem sap is about 7.5 to 8. Based on the pH measured by the indicator electrode probe 20 and the reference electrode probe 30, whether the tip portions of the probes 20, 30, and 40 are disposed in the phloem PH or disposed in the xylem XY can be determined. Based on this, an amount of stick of the probe 20, 30, or 40 can be adjusted.

Second Embodiment

Next, a vascular sap measurement sensor 2 according to the second embodiment of the present invention will be described. The vascular sap measurement sensor 2 has a function of measuring the electrical conductivity, in addition to the pH of vascular sap.

(Vascular Sap Measurement Sensor)

Figure 6:
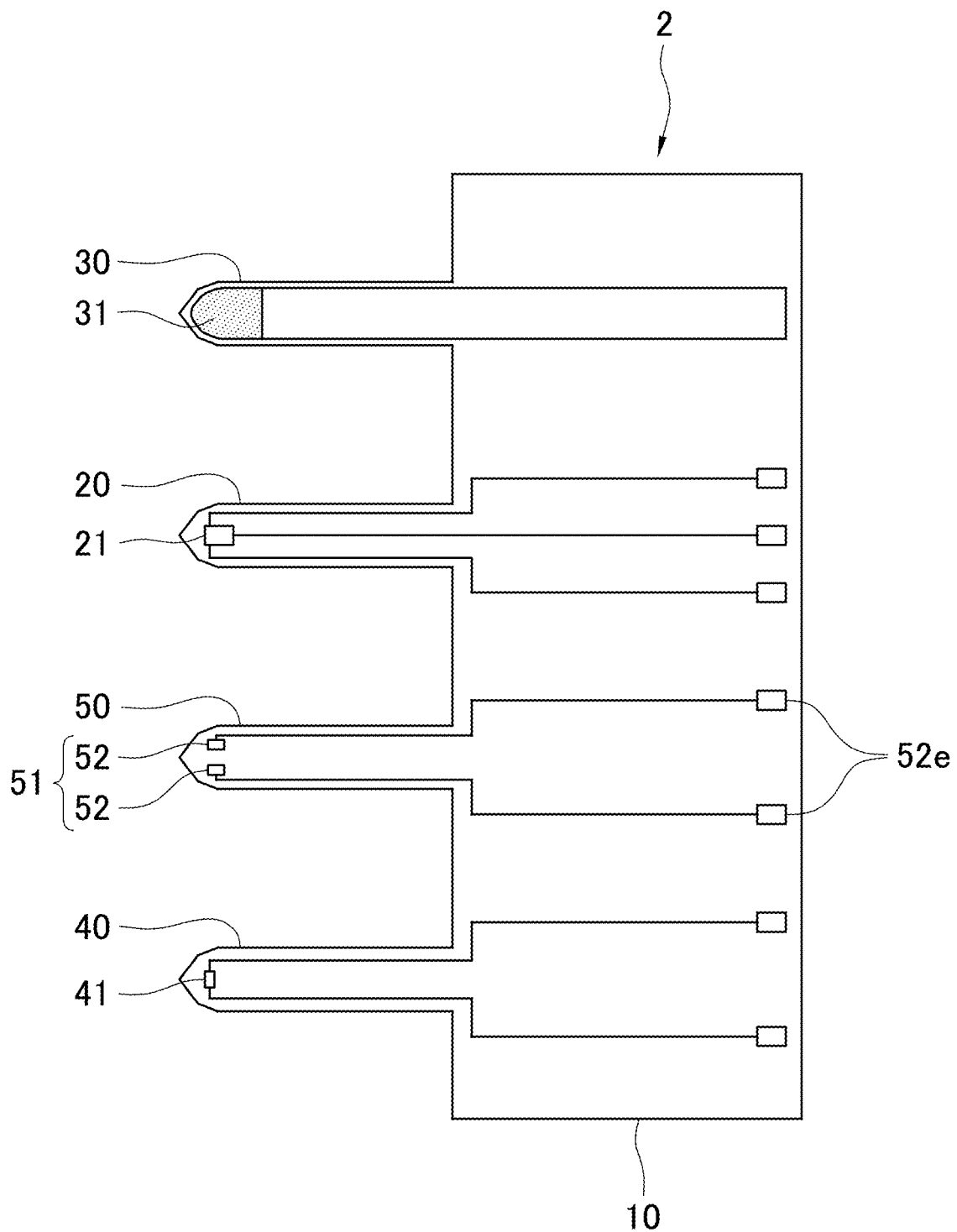
FIG. 6 is a plan view of a vascular sap measurement sensor according to a second embodiment.

As illustrated in FIG. 6, the vascular sap measurement sensor 2 of this embodiment is configured by adding an electrical conductivity probe 50 to the vascular sap measurement sensor 1 of the first embodiment. The configurations other than that are similar to those of the first embodiment, and therefore the same reference numerals are given to the same members and the description thereof will be omitted.

The electrical conductivity probe 50 is used for measurement of the electrical conductivity of vascular sap. The temperature of the vascular sap measured by the temperature probe 40 is used for temperature compensation of the electrical conductivity measurement value. Accordingly, in a case where the temperature compensation is unnecessary or the like, the temperature probe 40 need not be disposed in the vascular sap measurement sensor 2.

Electrical Conductivity Probe

The electrical conductivity probe 50 is arranged in parallel in the same plane together with the other probes 20, 30, and 40, and the base end of the electrical conductivity probe 50 is supported by the supporting portion 10. The order of arrangement of the probes 20, 30, 40 and 50 is not specifically limited. The electrical conductivity probe 50 has a shape and dimensions similar to those of the other probes 20, 30, and 40.

An electrical conductivity electrode pair 51 is disposed on the tip portion of the electrical conductivity probe 50. The electrical conductivity electrode pair 51 is formed of a pair of electrodes 52 and 52 disposed at a predetermined interval. The electrical conductivity electrode pair 51 measures the electrical conductivity of vascular sap present between the electrodes 52 and 52. As long as the electrode 52 can be disposed on the tip portion of the electrical conductivity probe 50, the size of the electrode 52 is not specifically limited. For example, an Al thin film can be used as the electrode 52.

On the top surface of the supporting portion 10, two electrode pads 52e coupled to the two electrodes 52 via wirings are disposed. The electrical conductivity can be measured by AC two-electrode method. That is, between the pair of electrode pads 52e and 52e corresponding to the pair of electrodes 52 and 52, an AC power supply and an ammeter are coupled in series. The AC power supply supplies a current between the electrodes 52 and 52, and the ammeter measures the current flowing between the electrodes 52 and 52. Based on the Ohm's law, the electrical resistance between the electrodes 52 and 52 is calculated from the current measured by the ammeter, and the electrical conductivity is obtained from the electrical resistance.

Generally, a range of the electrical conductivity of soil appropriate for raising a plant is from 0.1 to 1.5 mS/cm. The electrical conductivity of soil being 2.0 to 5.0 mS/cm generates a failure in the plant. It is inferred that the electrical conductivity of vascular sap in the plant is same extent of the electrical conductivity of soil or larger than that. To measure the electrical conductivity of vascular sap, it is preferred that the measurement range of the electrical conductivity includes 0.1 to 14 mS/cm.

In the AC two-electrode method, the electrical conductivity is expressed by Formula (1).

[Formula 1]

$$\sigma = \frac{K}{R} \quad (1)$$

Here, σ denotes the electrical conductivity [S/m], K denotes a cell constant [m$^{-1}$], and R denotes the electrical resistance [Ω] between the electrodes.

The electrical conductivity σ is obtained by dividing the cell constant K by an electrical resistance R as the measurement value. Therefore, the measurement range of the electrical conductivity by AC two-electrode method depends on the cell constant K of the electrode pair.

Figure 10:
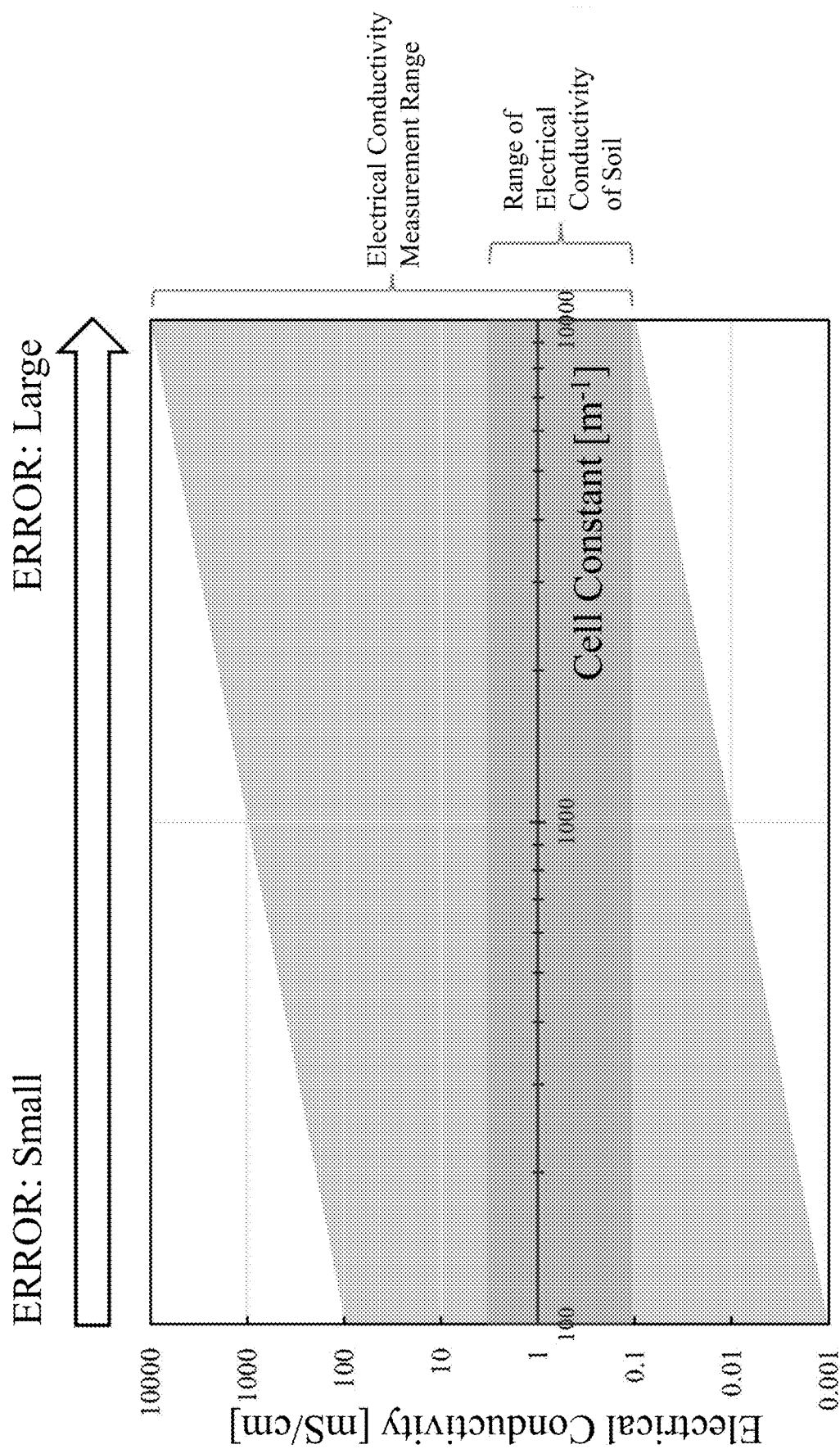
FIG. 10 is a graph illustrating a relationship between a cell constant K and a measurement range of the electrical conductivity.

The graph in FIG. 10 illustrates a general relationship between the cell constant K and the measurement range of the electrical conductivity. As seen from the graph in FIG. 10, even when the cell constant K is 10,000 m$^{-1}$, the electrical conductivity of vascular sap can be measured in theory. However, the larger the cell constant K is, the larger an error due to an influence of polarization becomes. Conversely, as the cell constant K decreases, the electrical conductivity can be accurately measured. For accurately measuring the electrical conductivity of vascular sap, the cell constant K of the electrical conductivity electrode pair 51 is preferably from 500 to 2,000 m$^{-1}$, and more preferably from 500 to 1,000 m$^{-1}$.

The cell constant K can be obtained by dividing an inter-electrode distance L by an electrode surface area S as shown in Formula (2).

[Formula 2]

$$K = \frac{L}{S} \quad (2)$$

To set the cell constant K to be a comparatively small value, such as 500 to 2,000 m$^{-1}$, the electrode surface area S needs to be increased. However, there is a limitation in increasing the surface area of the electrode 52 as the plane electrode disposed on the tip portion of the electrical conductivity probe 50 having a small area.

Figure 7:
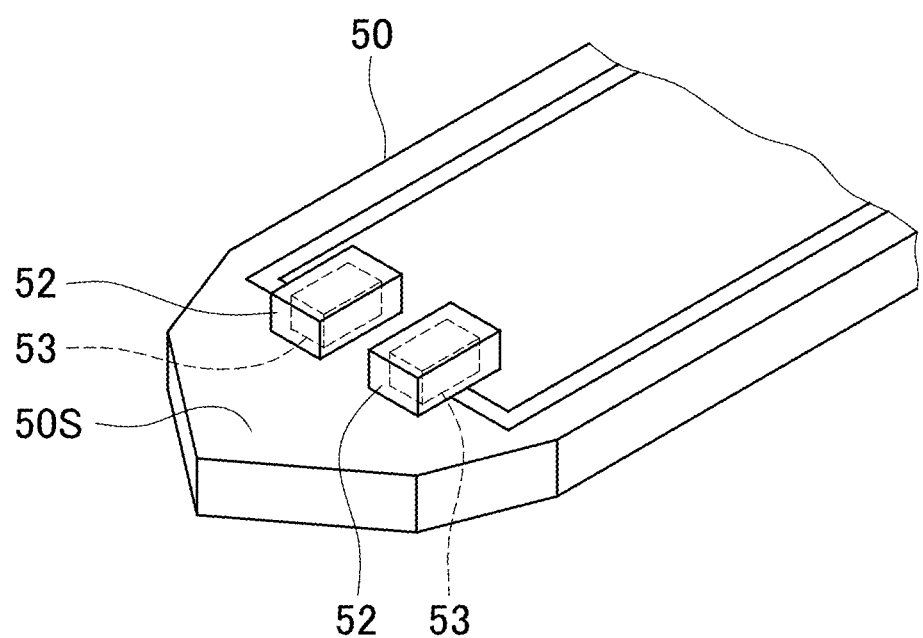
FIG. 7 is a perspective view of an electrical conductivity electrode pair.

Therefore, as illustrated in FIG. 7, the electrode 52 preferably has a three-dimensional shape. That is, each of the pair of electrodes 52 and 52 may be formed of a metal layer that covers a projection 53 formed on a probe surface 50S. The projection 53 formed on the probe surface 50S having a rectangular parallelepiped shape allows configuring the electrode 52 with five surfaces excluding the bottom surface and therefore the surface area can be increased by the amount. Thus, configuring the electrode 52 in the three-dimensional shape allows widening the electrode surface area. Accordingly, while the electrical conductivity electrode pair 51 has the size such that the electrical conductivity electrode pair 51 can be inserted into the plant, the cell constant K can be decreased.

The electrode 52 having the three-dimensional shape can be formed in, for example, the following procedure. A mask pattern to protect the electrode part is formed on the semiconductor substrate, and the projection 53 serving as the base of the three-dimensional electrode is formed by dry etching. Next, an oxide film is formed on the surface of the projection 53. Next, patterning is performed on a metal layer covering the surface of the projection 53, the wirings, and the electrode pads 52e with a metal thin film.

Figure 8:
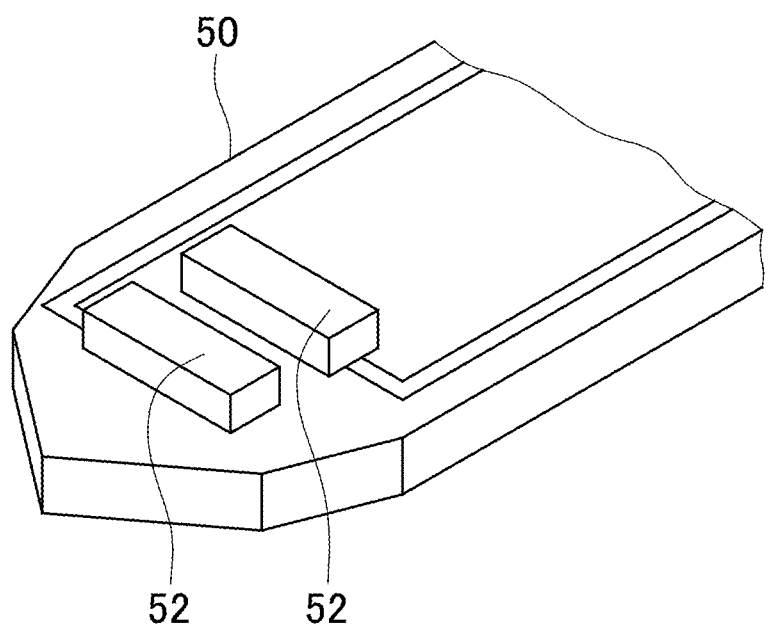
FIG. 8 is a perspective view of an electrical conductivity electrode pair of another configuration.

Note that in the example illustrated in FIG. 7, the pair of electrodes 52 and 52 are arranged side by side along the width direction of the electrical conductivity probe 50. Accordingly, the resistance when the electrical conductivity probe 50 is sticked to the plant can be comparatively decreased. Instead of this, as illustrated in FIG. 8, the pair of electrodes 52 and 52 may be arranged side by side along the axial direction of the electrical conductivity probe 50. Accordingly, a clearance between the electrodes 52 and 52 is disposed along the width direction of the electrical conductivity probe 50. Therefore, when the electrical conductivity probe 50 is sticked to the plant, the clearance between the electrodes 52 and 52 runs along a vascular bundle, and the vascular sap easily passes through.

(Measuring Method)

Next, the measuring method of the electrical conductivity of vascular sap by the vascular sap measurement sensor 2 will be described.

Figure 9:
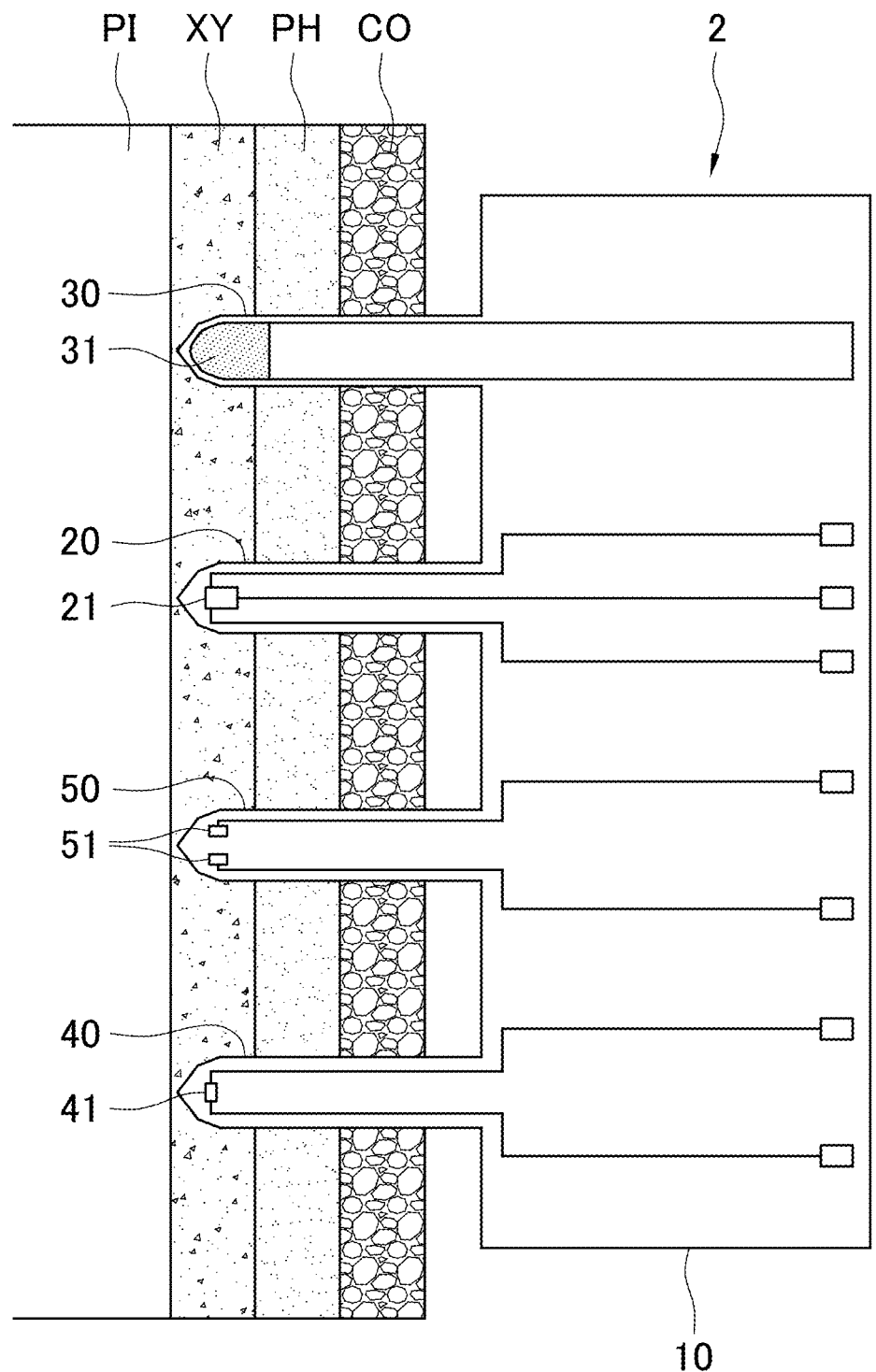
FIG. 9 is a use state explanatory view of the vascular sap measurement sensor according to the second embodiment.

As illustrated in FIG. 9, the vascular sap measurement sensor 2 is mounted by sticking all of the probes 20, 30, 40, and 50 to the plant. To measure the electrical conductivity of phloem sap, the tip portions of the probes 20, 30, 40, and 50 are disposed in the phloem PH. To measure the electrical conductivity of xylem sap, the tip portions of the probes 20, 30, 40, and 50 are disposed in the xylem XY.

As illustrated in FIG. 9, disposing the tip portion of the electrical conductivity probe 50 in the xylem XY brings the electrical conductivity electrode pair 51 into contact with the xylem sap. Therefore, the electrical conductivity electrode pair 51 can measure the electrical conductivity of xylem sap.

The electrical conductivity measurement value obtained by the electrical conductivity electrode pair 51 depends on the temperature. Generally, the electrical conductivity measurement value changes by 1 to 3% per 1° C. Therefore, performing temperature compensation on the electrical conductivity measurement value is preferred. Disposing the tip portion of the temperature probe 40 in the xylem XY brings the temperature sensor 41 into contact with the xylem sap.

Therefore, the temperature sensor 41 can measure the temperature of the xylem sap. Based on the temperature of the xylem sap measured by the temperature probe 40, temperature compensation is performed on the electrical conductivity measurement value. This allows accurately measuring the electrical conductivity of xylem sap.

The temperature compensation of the electrical conductivity measurement value is performed in, for example, the following procedure. That is, based on Formula (3), the electrical conductivity measurement value is converted into electrical conductivity $\sigma_{25}$ [S/m] at a reference temperature 25° C. Here, α denotes a temperature coefficient, T denotes a temperature [° C.] of a measurement target liquid, and σ denotes an electrical conductivity measurement value [S/m].

[Formula 3]

$$\sigma_{25} = \alpha|25 - T|\sigma \qquad (3)$$

The temperature coefficient α is obtained by Formula (4). Here, $T_1$ denotes a temperature [° C.] other than 25° C. or $T_2$, $T_2$ denotes a temperature [° C.] other than 25° C. or $T_1$, $\sigma_1$ denotes an electrical conductivity measurement value [S/m] at $T_1$, and $\sigma_2$ denotes an electrical conductivity measurement value [S/m] at $T_2$.

[Formula 4]

$$\alpha = \frac{(\sigma_1 - \sigma_2)}{[\sigma_2(T_1 - 25) - \sigma_1(T_2 - 25)]} \qquad (4)$$

As described above, the vascular sap measurement sensor 2 can measure the electrical conductivity of xylem sap. A fertilizer sprayed on the soil is decomposed into salt content, such as nitrate nitrogen, by microorganism. A salinity concentration and the electrical conductivity have a positive correlation. Therefore, measuring the electrical conductivity of xylem sap allows quantifying the nutritional substance taken in the plant.

Note that disposing the tip portion of the electrical conductivity probe 50 in the phloem PH allows measuring the electrical conductivity of phloem sap. Since the xylem sap contains salt content, such as nitrate nitrogen, the xylem sap has a property of electrical conductivity higher than that of water contained in other parts (for example, the skin layer CO, the phloem PH, and the pith PI). Using this, whether the tip portion of the probe 50 is disposed in the phloem PH or disposed in the xylem XY can be determined. Based on this, an amount of stick of the probe 20, 30, 40, or 50 can be adjusted.

All of the probes 20, 30, 40, and 50 of the vascular sap measurement sensor 2 of this embodiment have the approximately same lengths. The indicator electrode 21, the solid reference electrode 31, the temperature sensor 41, and the electrical conductivity electrode pair 51, which are disposed on the tip portions of the probes 20, 30, 40, and 50, are disposed at the approximately same position in the sticking direction to the plant as the measurement target (the axial direction of the respective probes 20, 30, 40, and 50). Therefore, the elements 21, 31, 41, and 51 can be disposed in the phloem PH and can be disposed in the xylem XY, at the same time.

Since the elements 21, 31, 41, and 51 are disposed at the same position in the sticking direction to the plant, the pH and the electrical conductivity of phloem sap or xylem sap of the plant can be simultaneously measured. It is considered that each of the pH and the electrical conductivity of vascular sap has a range appropriate for raising a plant. The pH of vascular sap outside the appropriate range tends to cause the plant to get a disease. The electrical conductivity of vascular sap outside the appropriate range negatively affects the growth of the plant. Simultaneous measurement of the pH and the electrical conductivity of vascular sap allows quantitatively monitoring the health condition of the plant.

The temperature of the vascular sap measured by the temperature probe 40 is used for temperature compensation of the electrical conductivity measurement value and temperature compensation of the pH measurement value.

The vascular sap measurement sensor 2 may include only the electrical conductivity probe 50 or only the electrical conductivity probe 50 and the temperature probe 40 and need not include the indicator electrode probe 20 or the reference electrode probe 30. The vascular sap measurement sensor 2 having the configuration allows measuring the electrical conductivity of vascular sap.

Third Embodiment

Next, a vascular sap measurement sensor 3 according to the third embodiment of the present invention will be described.

Figure 11:
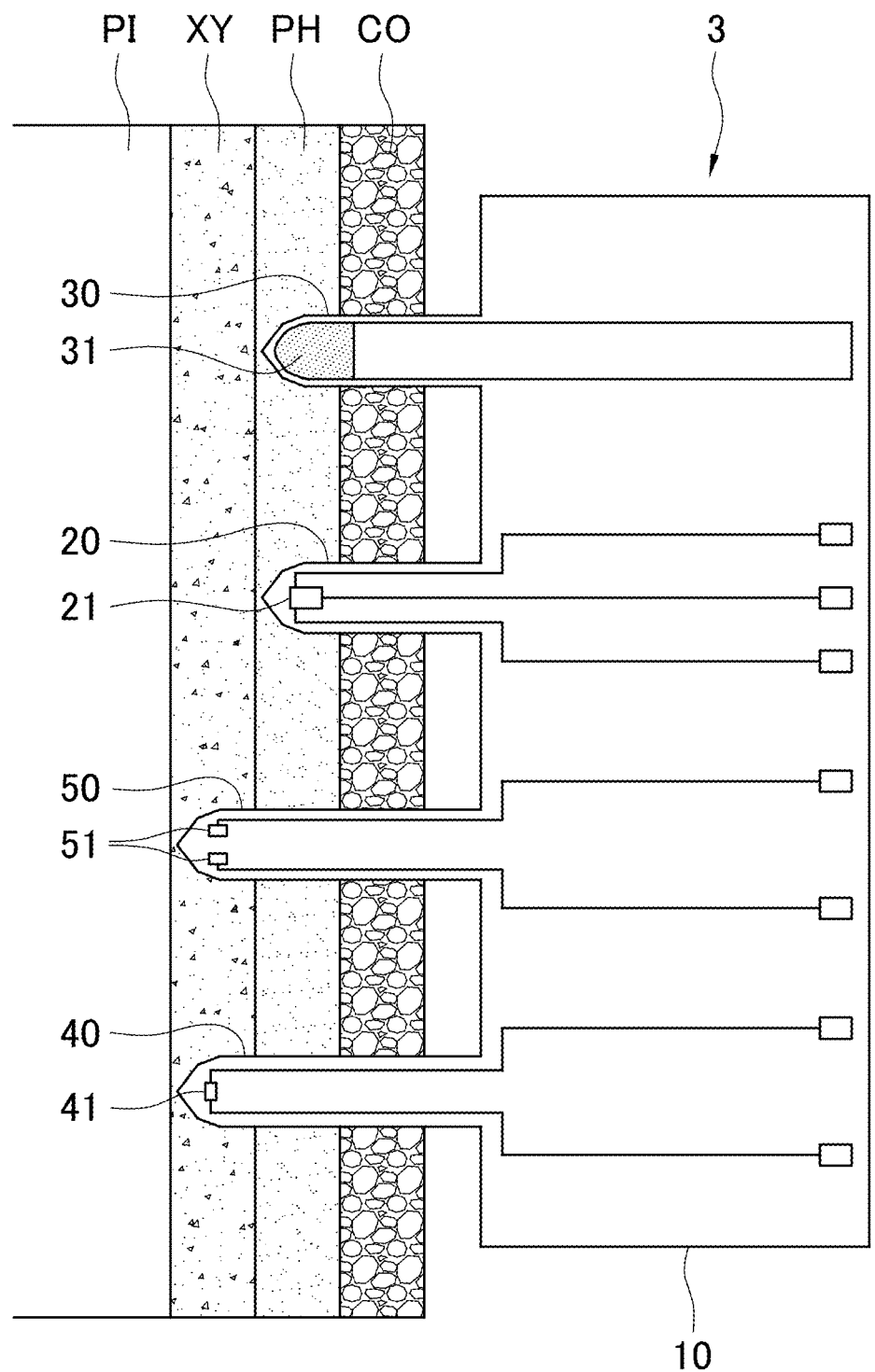
FIG. 11 is a plan view of a vascular sap measurement sensor according to a third embodiment.

As illustrated in FIG. 11, with the vascular sap measurement sensor 3 of this embodiment, electrical conductivity probe 50 is configured to be longer than the indicator electrode probe 20 and the reference electrode probe 30 in the vascular sap measurement sensor 2 of the second embodiment.

Specifically, the length of the electrical conductivity probe 50 is configured to be longer than the lengths of the indicator electrode probe 20 and the reference electrode probe 30 by a distance between the center of the phloem PH and the center of the xylem XY of the plant as the measurement target. Although depending on the kind of the plant as the measurement target and the thickness of the stem, the difference in length is, for example, from 50 to 300 µm.

The indicator electrode 21, the solid reference electrode 31, and the electrical conductivity electrode pair 51 are disposed on the tip portions of the probes 20, 30, and 50, respectively. Therefore, the indicator electrode 21 and the solid reference electrode 31 are disposed at positions different from the electrical conductivity electrode pair 51 in the sticking direction to the plant. Then, the electrical conductivity electrode pair 51 is disposed so as to reach the position in the plant deeper than the indicator electrode 21 and the solid reference electrode 31.

When the probes 20, 30, and 50 are sticked to the plant and the electrical conductivity electrode pair 51 is disposed in the xylem XY, the indicator electrode 21 and the solid reference electrode 31 are disposed in the phloem PH. In other words, the distance from the electrical conductivity electrode pair 51 to the indicator electrode 21 and the solid reference electrode 31 is configured such that the indicator electrode 21 and the solid reference electrode 31 are disposed in the phloem PH while the electrical conductivity electrode pair 51 is disposed in the xylem XY.

With the configuration, the vascular sap measurement sensor 3 can measure the electrical conductivity of xylem sap while measuring the pH of phloem sap.

Fourth Embodiment

Next, a vascular sap measurement sensor 4 according to the fourth embodiment of the present invention will be described. The vascular sap measurement sensor 4 has a function of measuring a water dynamics, in addition to the pH and the electrical conductivity of vascular sap.

(Vascular Sap Measurement Sensor)

Figure 12:
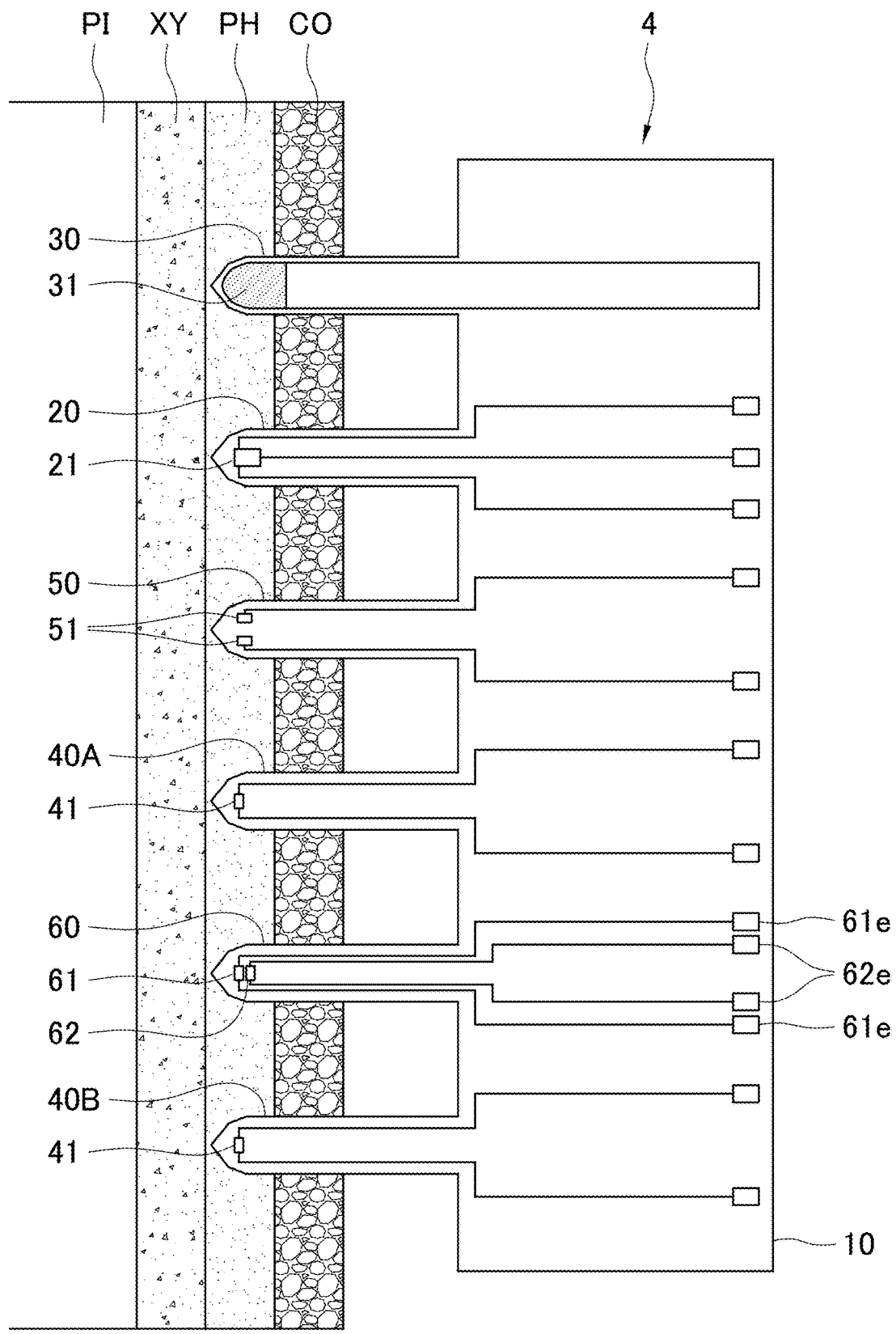
FIG. 12 is a plan view of a vascular sap measurement sensor according to a fourth embodiment.

As illustrated in FIG. 12, in the vascular sap measurement sensor 4 of this embodiment, the temperature probe 40 is configured as two of a first temperature probe 40A and a second temperature probe 40B, and a heater-equipped temperature probe 60 is added to the vascular sap measurement sensor 2 of the second embodiment. The configurations other than those are similar to those of the second embodiment, and therefore the same reference numerals are given to the same members and the description thereof will be omitted.

The first and second temperature probes 40A and 40B and the heater-equipped temperature probe 60 are used for measurement of a dynamics of vascular sap in combination. The temperature of the vascular sap measured by the first temperature probe 40A or the second temperature probe 40B is also used for temperature compensation of the pH measurement value and the electrical conductivity measurement value.

The first and second temperature probes 40A and 40B and the heater-equipped temperature probe 60 are arranged in parallel in the same plane, and the base ends of the first and second temperature probes 40A and 40B and the heater-equipped temperature probe 60 are supported by the supporting portion 10 together with the other probes 20, 30, and 50. The first and second temperature probes 40A and 40B are disposed at positions across the heater-equipped temperature probe 60. Additionally, the first and second temperature probes 40A and 40B and the heater-equipped temperature probe 60 have shapes and dimensions similar to those of the other probes 20, 30, and 50.

Temperature Probe

The first and second temperature probes 40A and 40B each have configurations similar to the temperature probe 40 of the first embodiment. That is, each of the first and second temperature probes 40A and 40B includes the temperature sensor 41 on the tip portion. The temperature sensor 41 can measure the temperature of the vascular sap.

Heater-Equipped Temperature Probe

A temperature sensor 61 is disposed on the tip portion of the heater-equipped temperature probe 60. As the temperature sensor 61, the temperature sensor similar to the temperature sensor 41 of the temperature probe 40 can be used. On the top surface of the supporting portion 10, two electrode pads 61e coupled to the temperature sensor 61 via wiring are disposed. The temperature can be measured by the temperature sensor 61 by the method similar to that of the temperature sensor 41 of the temperature probe 40.

The heater-equipped temperature probe 60 includes a heater 62. The heater 62 only needs to supply heat to the heater-equipped temperature probe 60, and the position is not limited to the tip portion. As long as the heater 62 can be disposed on the heater-equipped temperature probe 60, the size of the heater 62 is not specifically limited. For example, a pn junction diode formed using an oxidation diffusion furnace can be employed as the heater 62. The heater 62 may be formed by forming a thin film of platinum (Pt), nichrome (NiCr), or an indium tin oxidation material (ITO) by, for example, sputtering method and evaporation method and processing the thin film in a predetermined shape.

On the top surface of the supporting portion 10, two electrode pads 61e coupled to the heater 62 via wiring are disposed. A DC constant voltage source is coupled between the two electrode pads 61*e* and 61*e*. A constant voltage is supplied to the heater 62 as the pn junction diode by the DC constant voltage source in the forward direction. Flowing a current through the heater 62 allows generating heat.

(Measuring Method)

Next, the measuring method of the dynamics of the vascular sap by the vascular sap measurement sensor 4 will be described.

As illustrated in FIG. 12, all of the probes 20, 30, and 40A, 40B, 50, and 60 of the vascular sap measurement sensor 4 are sticked and mounted to the plant. To measure the dynamics of the phloem sap, the tip portions of the first and second temperature probes 40A and 40B and the heater-equipped temperature probe 60 are disposed in the phloem PH. To measure the dynamics of the xylem sap, the tip portions of the first and second temperature probes 40A and 40B and the heater-equipped temperature probe 60 are disposed in the xylem XY.

Hereinafter, the case of measuring the dynamics of the phloem sap will be described.

First, the heater 62 disposed on the heater-equipped temperature probe 60 is operated. Upon operation of the heater 62, heat energy supplied from the heater 62 is supplied to the heater-equipped temperature probe 60. The heat energy supplied to the heater-equipped temperature probe 60 is emitted from the surface of the heater-equipped temperature probe 60 to the phloem sap flowing the inside of the phloem PH.

The temperature sensors 41, 41, and 61 measure the temperatures of the first and second temperature probes 40A and 40B and the heater-equipped temperature probe 60 at the time. Then, through comparison of the temperatures of the first temperature probe 40A and the second temperature probe 40B, the direction of the phloem flow is identified.

The first and second temperature probes 40A and 40B are disposed at positions across the heater-equipped temperature probe 60. When the phloem sap flows from the end to the root of the plant, the second temperature probe 40B positioned at the root side is warmed by the phloem sap whose temperature has been risen by the heater-equipped temperature probe 60 and the temperature of the second temperature probe 40B becomes higher than the temperature of the first temperature probe 40A at the end side.

Conversely, when the phloem sap flows from the root to the end of the plant, the first temperature probe 40A positioned at the end side is warmed by the phloem sap whose temperature has been risen by the heater-equipped temperature probe 60 and the temperature of the first temperature probe 40A becomes higher than the temperature of the second temperature probe 40B at the root side.

That is, the direction of the phloem flow can be identified as the direction heading from the temperature probe 40A or 40B having a low temperature to the temperature probe 40B or 40A having a high temperature.

Generally, the xylem flow is in the direction heading from the root to the end of the plant, but the direction of the phloem flow cannot be grasped from the outer shape of the plant. However, the vascular sap measurement sensor 4 allows identifying the direction of the phloem flow.

Next, from the temperatures measured by the first and second temperature probes 40A and 40B and the heater-equipped temperature probe 60, the flow rate of the phloem sap is measured based on Granier method. Here, calculation is performed based on the temperature difference between the temperature probe 40A or 40B whose temperature is low among the first and second temperature probes 40A and 40B and the heater-equipped temperature probe 60. The temperature probe 40A or 40B having the lower temperature is disposed on the upstream of the phloem flow with respect to the heater-equipped temperature probe 60.

For example, when the flow rate of the phloem sap is large (a flow velocity is fast), the phloem sap at the proximity of the heater-equipped temperature probe 60 is always replaced by the new phloem sap. Therefore, making the heat energy supplied to the heater-equipped temperature probe 60 constant lowers the temperature of the heater-equipped temperature probe 60. On the other hand, when the flow rate of the phloem sap is small (the flow velocity is slow), the phloem sap at the proximity of the heater-equipped temperature probe 60 is accumulated. Therefore, making the heat energy supplied to the heater-equipped temperature probe 60 constant rises the temperature of the heater-equipped temperature probe 60.

Accordingly, the flow velocity of the phloem sap can be obtained from a temperature difference $\Delta T$ between the temperature probe 40A or 40B and the heater-equipped temperature probe 60. Specifically, as shown by Formula (5), the temperature difference $\Delta T$ becomes a function of a flow velocity u. Based on the function, the flow velocity u can be calculated from the temperature difference $\Delta T$.

[Formula 5]

$$u = \frac{1}{\alpha}\left\{\frac{\Delta T(0) - \Delta T(u)}{\Delta T(u)}\right\}^{\frac{1}{\beta}} \quad (5)$$

Here, u indicates an average flow velocity [m/s], $\Delta T(u)$ indicates a temperature difference [° C.] between the temperature probe 40 and the heater-equipped temperature probe 60 when the average flow velocity is u, $\Delta T(0)$ indicates the maximum temperature [° C.] of $\Delta T$, and $\alpha$ and $\beta$ indicate coefficients obtained from the observation data.

Additionally, based on Formula (6), a flow rate F can be calculated from the flow velocity u.

[Formula 6]

$$F = u \times S \quad (6)$$

Here, F indicates the flow rate [m³/s], and S indicates a cross-sectional area [m²] of the xylem or the phloem.

Note that when the tip portions of the first and second temperature probes 40A and 40B and the heater-equipped temperature probe 60 are disposed in the xylem XY of the plant, the flow velocity and the flow rate of the xylem sap can be obtained together with the direction of the xylem flow. Additionally, the vascular sap measurement sensor 4 can measure the flow rate of vascular sap also by heat pulse method.

The vascular sap measurement sensor 4 of this embodiment can measure the pH and the electrical conductivity of vascular sap together with the flow rate of vascular sap. That is, the water dynamics and the nutritional substance dynamics of the plant can be simultaneously measured. To raise the plant, the balance between the water content and the nutritional substance is important. For example, too many nutritional substances with respect to the water content causes fertilizer burn due to excessive nutrient. Simultaneously measuring the water dynamics and the nutritional substance dynamics of the plant allows maintaining the balance between the water content and the nutritional substance.

Forming the vascular sap measurement sensor 4 with the semiconductor substrate allows downsizing the vascular sap measurement sensor 4 and miniaturizing the probes 20, 30, 40A, 40B, 50, and 60. Therefore, even when the vascular sap measurement sensor 4 is installed to the plant, damage (injury) given to the plant can be decreased, and the vascular sap measurement sensor 4 can be installed over a long period of time. This allows monitoring the water dynamics and the nutritional substance dynamics of the plant over a long period of time, and water can be sprinkled and the nutrient can be supplied at the appropriate timings according to the growing conditions of the plant. Consequently, a yield of, for example, crops and tree-fruits can be increased. Moreover, because of reduction in poor growth including a disease, high-value added cultivation, such as high-quality tree-fruit cultivation (sugar content of the fruit is high) and stable production (the quality is the same), is possible.

The temperature probe 40 disposed on the vascular sap measurement sensor 4 may be one. The configuration also allows measuring the flow rate of vascular sap. Additionally, the electrical conductivity probe 50 need not be disposed on the vascular sap measurement sensor 4. That is, the vascular sap measurement sensor 4 may be a combination of the indicator electrode probe 20 and the reference electrode probe 30 for pH measurement and the first and second temperature probes 40A and 40B and the heater-equipped temperature probe 60 for water dynamics measurement. The vascular sap measurement sensor 4 need not include the indicator electrode probe 20 or the reference electrode probe 30. That is, the vascular sap measurement sensor 4 may be a combination of the electrical conductivity probe 50 for electrical conductivity measurement and the first and second temperature probes 40A and 40B and the heater-equipped temperature probe 60 for water dynamics measurement.

Working Examples (pH Measurement)
Surface Shape Evaluation of Solid Reference Electrode A solid reference electrode was formed on a glass piece. Here, the solid reference electrode had a stacked structure of a base layer, a silver chloride layer, and a chloride layer. A gold thin film was formed on the glass piece to form the base layer. Silver chloride ink was applied over the surface of the base layer and dried to form the silver chloride layer. Potassium chloride powder and a glass paste were mixed, and after the mixture was applied over the surface of the silver chloride layer, the mixture was fired (500° C., 60 minutes) to form the chloride layer.

Four patterns of a weight ratio between the glass paste and the potassium chloride, 1:1, 0.75, 0.50, and 0.25, were set, and samples were manufactured using the respective patterns. Then, the surface shape of each sample was observed.

When the weight ratio between the glass paste and the potassium chloride was 1:1 and 1:0.75, peeling and a crack of the chloride layer were observed. When the weight ratio between the glass paste and the potassium chloride was 1:0.50 and 1:0.25, no failure in appearance was observed.

Thus, it has been confirmed that the smaller the ratio of the potassium chloride to the glass paste is, the higher the adhesiveness of the chloride layer is. Specifically, setting 0.50 or less of the potassium chloride to the glass paste of 1 allows obtaining the sufficient adhesiveness.
Material Stability Evaluation of Solid Reference Electrode The material stability of each sample obtained above was evaluated. After the solid reference electrode and the metal electrode were immersed in pure water for 18 hours, appearance observation was performed using a SEM and a microscope for evaluation.

Consequently, when the weight ratio between the glass paste and the potassium chloride was set to be 1:1, 0.75, or 0.50, dissolution of the glass paste was observed. When the weight ratio between the glass paste and the potassium chloride was set to be 1:0.25, dissolution of the glass paste was not observed. Thus, it has been confirmed that setting the potassium chloride of 0.25 or less to the glass paste of 1 allows inhibiting dissolution of the glass paste.

As described above, it has been confirmed that setting the potassium chloride of 0.25 or less to the glass paste of 1 allows obtaining the chloride layer that has good adhesiveness and in which the glass paste is less likely to be dissolved.
Output Potential Evaluation of Solid Reference Electrode Next, a solid reference electrode was formed on a silicon substrate. The solid reference electrode was formed in the procedure similar to the above-described procedure. Two patterns of a weight ratio between the glass paste and the potassium chloride, 1:0.25 and 0.10, were set, and samples were manufactured using the respective patterns. A sample in which the weight ratio between the glass paste and the potassium chloride is 1:0.25 is a sample 1, and a sample in which the weight ratio between the glass paste and the potassium chloride is 1:0.10 is a sample 2.

Figure 13A:
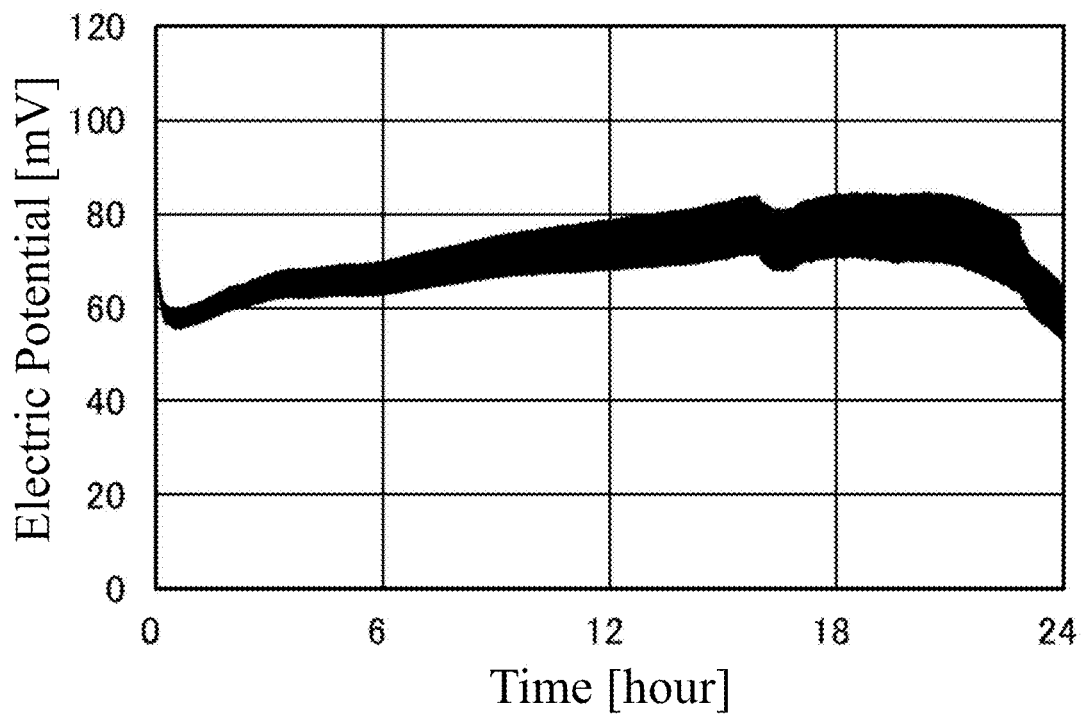
FIG. 13A is a graph illustrating a time change of an output potential of a sample 1.
Figure 13B:
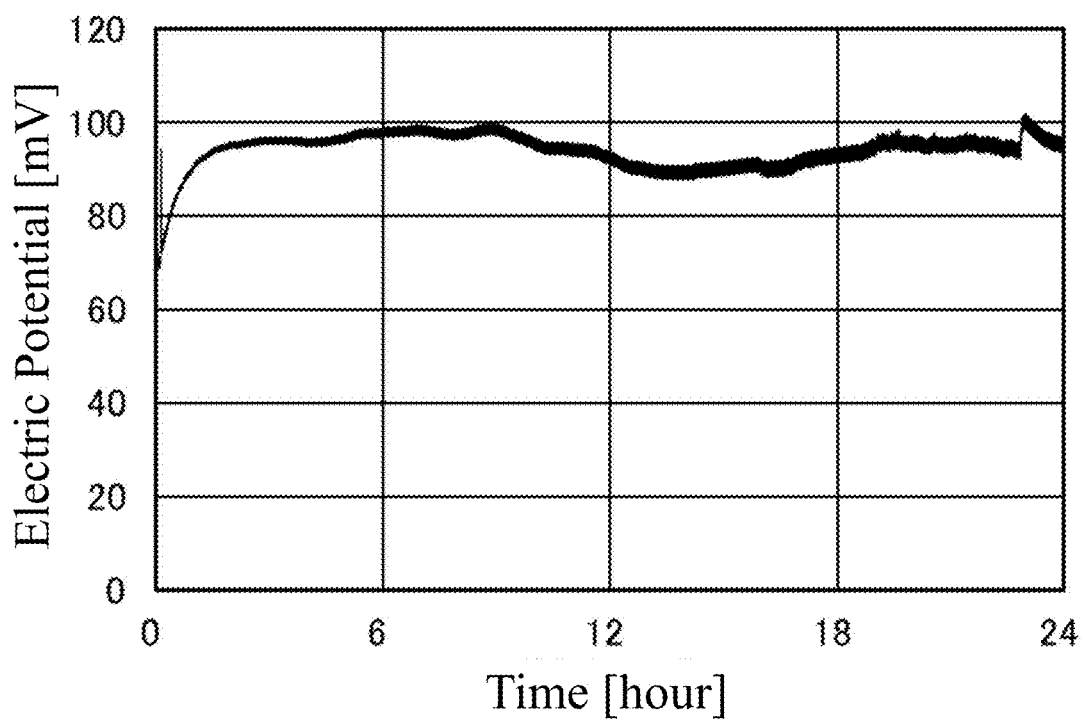
FIG. 13B is a graph illustrating a time change of an output potential of a sample 2.

The output potentials of the samples 1 and 2 were evaluated. The solid reference electrode and the metal electrode were dipped in pure water, and the electric potential between the electrodes was measured for 24 hours for evaluation. FIG. 13A illustrates a time change of the output potential of the sample 1. FIG. 13B illustrates a time change of the output potential of the sample 2.

In comparison between the sample 1 and the sample 2, while a drift of the output potential is observed in the sample 1, a drift of the output potential is hardly observed in the sample 2. Thus, it has been confirmed that setting the potassium chloride of 0.10 or less to the glass paste of 1 stabilizes the output potential of the solid reference electrode.
Evaluation for pH Measurement A silicon substrate was processed to manufacture a vascular sap measurement sensor including an indicator electrode probe and a reference electrode probe. An ion-sensitive field effect transistor was disposed on the tip portion of the indicator electrode probe as an indicator electrode. Additionally, a solid reference electrode was disposed on the tip portion of the reference electrode probe. The solid reference electrode was formed in the procedure similar to the above-described procedure. Here, a weight ratio between a glass paste and potassium chloride was set to be 1:0.10. This vascular sap measurement sensor is Working Example 1.

Figure 14:
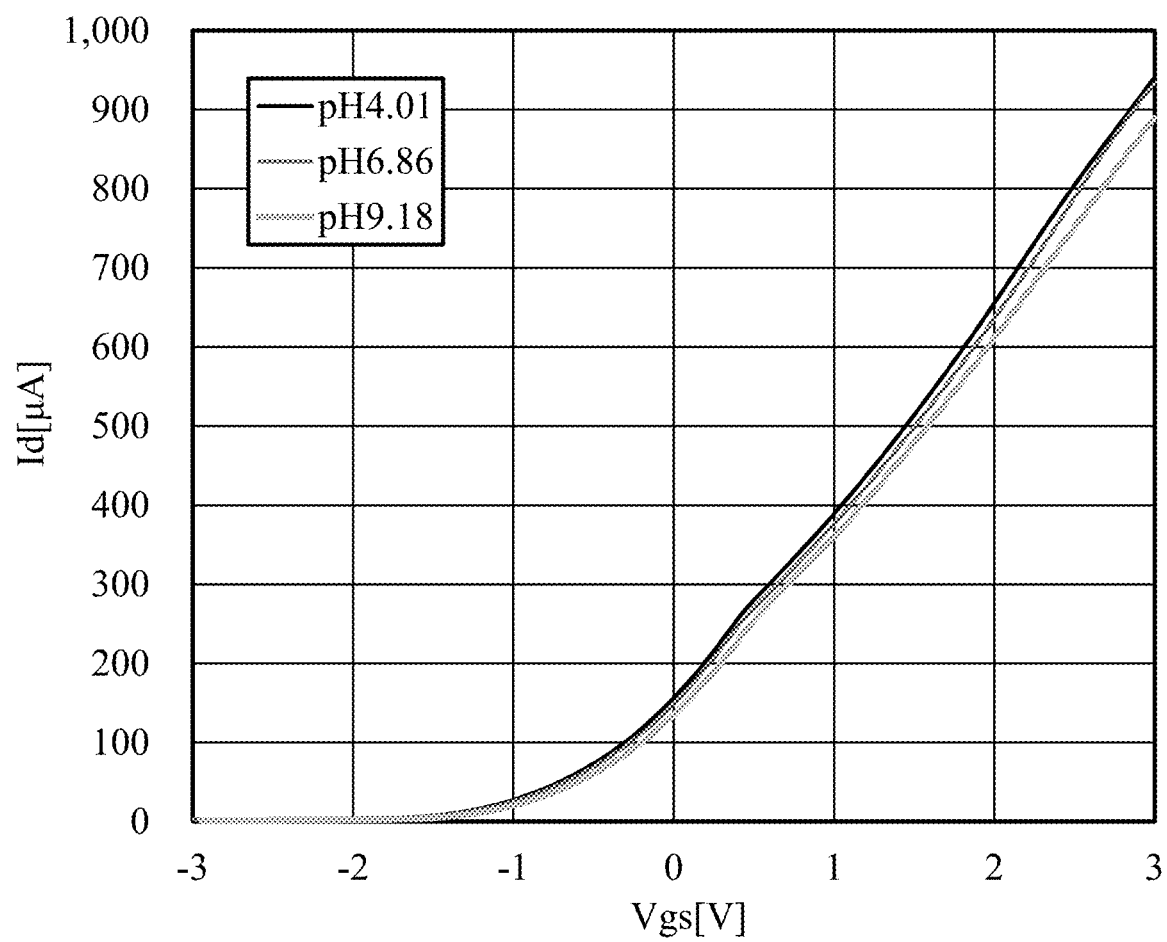
FIG. 14 is a graph illustrating a relationship between a gate-source voltage Vgs and a drain current Id of an ion-sensitive field effect transistor.

The indicator electrode and the solid reference electrode of Working Example 1 were dipped in a pH standard solution (pH: 4.01, 6.86, or 9.18) to measure the pH in a darkroom. FIG. 14 illustrates a relationship between the gate-source voltage Vgs and a drain current Id of the ion-sensitive field effect transistor.

As seen from FIG. 14, the Id-Vgs characteristic changes depending on the pH. Thus, it was confirmed that the pH was able to be measured with the indicator electrode and the solid reference electrode of Working Example 1. Additionally, sensor sensitivity was obtained as a change in Vgs per pH, and it was 29 mV/pH.
(Electrical Conductivity Measurement)

A silicon substrate was processed to manufacture a vascular sap measurement sensor including an electrical conductivity probe. An electrical conductivity electrode pair was disposed on a tip portion of the electrical conductivity probe. The electrical conductivity electrode pair formed of a pair of plane electrodes is Working Example 2. The plane electrode has a size 55 μm in the lateral direction and 100 μm in the vertical direction. The electrical conductivity electrode pair formed of a pair of three-dimensional electrodes is Working Example 3. The three-dimensional electrode has a rectangular parallelepiped shape and has a size of 55 μm in the lateral direction, 100 μm in the vertical direction, and 50 μm in height.

Cell Constant

The cell constant of the electrical conductivity electrode pair of each of Working Examples 2 and 3 was measured. For measurement, a KCl standard solution whose electrical conductivity was adjusted to be 1.41 mS/cm was used. The electrical conductivity probe was immersed in the KCl standard solution, and a resistance value of the standard solution was obtained from measurement values of a current and a voltage between the electrodes. 1.41 mS/cm was assigned for 6 and the obtained resistance value was assigned for R in Formula (1) to obtain the cell constant K. The cell constant was identified from the average value of the 10-times measurements.

The cell constant of the electrical conductivity electrode pair of Working Example 2 including the plane electrodes was 4,659 $m^{-1}$. The cell constant of the electrical conductivity electrode pair of Working Example 3 including the three-dimensional electrodes was 1,258 $m^{-1}$. Thus, it has been confirmed that the electrodes having the three-dimensional shape allows decreasing the cell constant of the electrical conductivity electrode pair.

Electrical Conductivity Measurement

An electrical conductivity of a potassium chloride solution was measured using Working Example 3. Potassium chloride solutions having concentrations different in units of 0.01 mol/L per were used for the measurement. The electrical conductivity of the potassium chloride solution at each concentration was measured. Using a commercially available sensor (LAQUAtwin B-771 manufactured by HORIBA), the electrical conductivities of the potassium chloride solutions were similarly measured.

Figure 15:
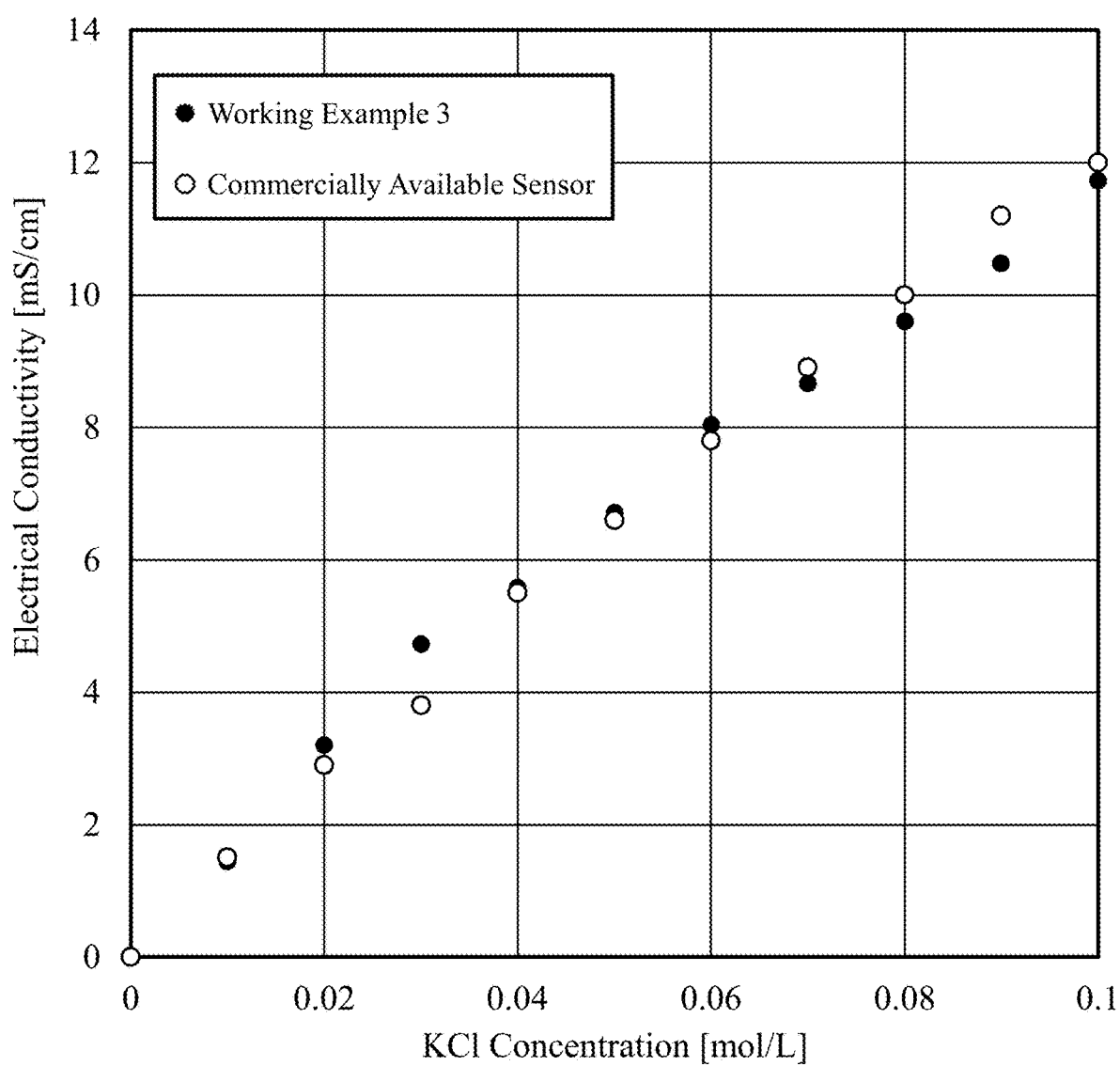
FIG. 15 is a graph illustrating a relationship between a concentration of a potassium chloride aqueous solution and an electrical conductivity measurement value.

FIG. 15 illustrates a relationship between the concentration of the potassium chloride aqueous solution and the electrical conductivity measurement value. The measurement value of the electrical conductivity obtained in Working Example 3 well matches the measurement value obtained by the commercially available sensor. At least, the measurement values of the electrical conductivity hardly differ between Working Example 3 and the commercially available sensor in the range of 0 to 12 mS/cm. Accordingly, it was confirmed that at least the electrical conductivity was able to be accurately measured in the range of 0 to 12 mS/cm in Working Example 3.

(Test Using a Plant)

A silicon substrate was processed to manufacture a vascular sap measurement sensor including an electrical conductivity probe and a temperature probe. First, using the KCl standard solution, a cell constant of the electrical conductivity electrode pair was measured in the procedure similar to the above-described procedure. Next, the electrical conductivity probe and the temperature probe were sticked to a stem of a cucumber grown in a plant pot to mount the sensors. The cucumber was put in a meteorological instrument together with the plant pot, the temperature was set to be 25° C., the humidity was set to be 70%, and the carbon dioxide concentration was set to be 500 ppm. The light intensity inside the meteorological instrument was changed according to the actual time. Simultaneously with this, the electrical conductivity was measured by the sensor.

Figure 16:
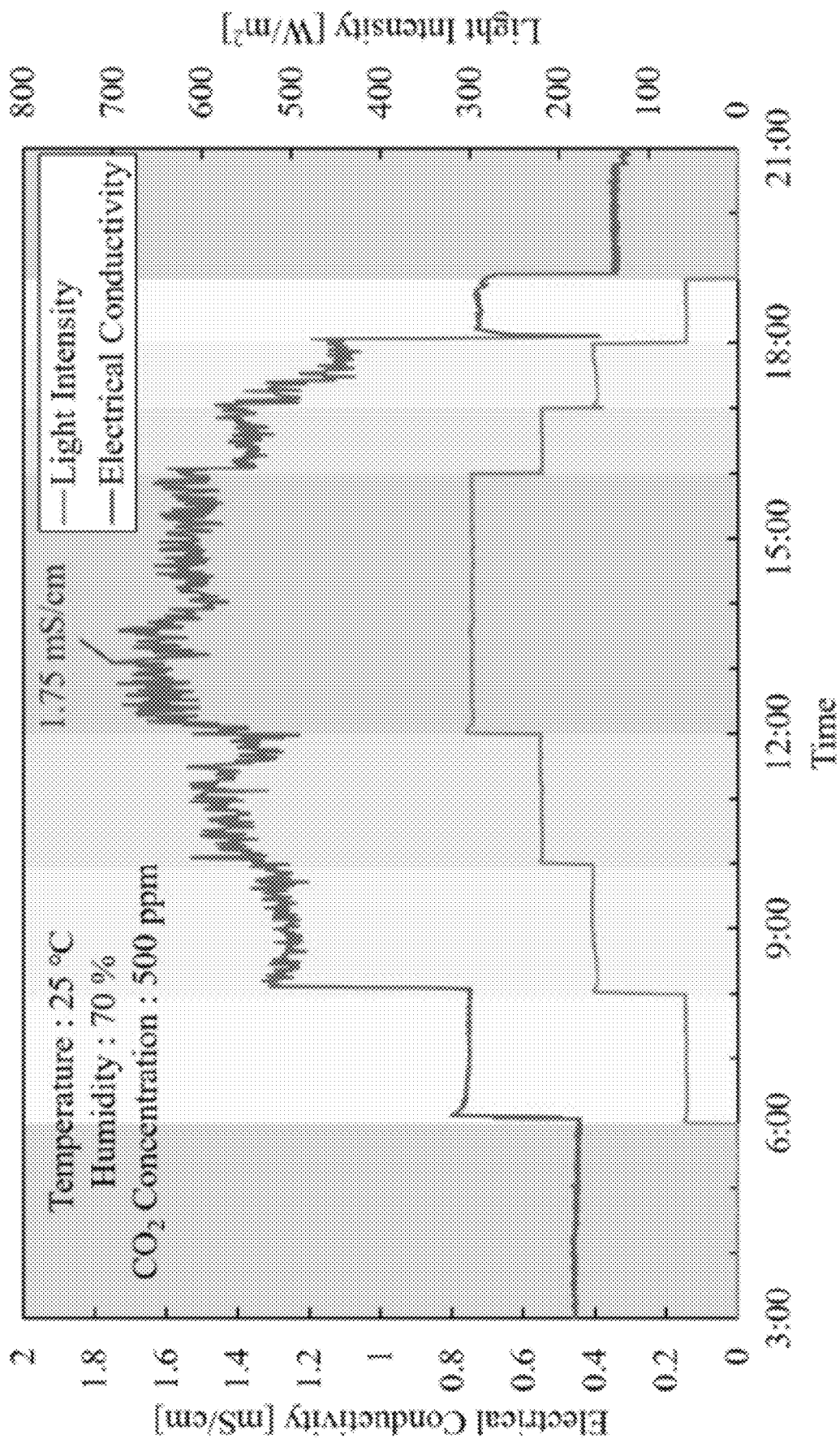
FIG. 16 is a graph illustrating a light intensity inside a meteorological instrument and a time change of the electrical conductivity measured by a sensor.

FIG. 16 illustrates the light intensity inside the meteorological instrument and the time change of the electrical conductivity measured by the sensor. It is seen from the graph in FIG. 16 that the increase in light intensity increases the electrical conductivity and the decrease in light intensity lowers the electrical conductivity. In accordance with the increase in light intensity, an amount of nitrate nitrogen that the plant absorbs from the soil increases. It is considered that the electrical conductivity measured by the sensor changed by the absorbing amount of nitrate nitrogen of the plant.

When the electrical conductivity of water came out of the plant pot was measured by the commercially available sensor, it was 1.78 mS/cm. The maximum value of the electrical conductivity measured by this sensor is 1.75 mS/cm, which is the approximately same value as the electrical conductivity of soil. Thus, it has been confirmed that this sensor can measure the nutritional substance dynamics of the plant.

REFERENCE SIGNS LIST 1, 2, 3, 4 vascular sap measurement sensor
10 supporting portion
20 indicator electrode probe
21 indicator electrode
30 reference electrode probe
31 solid reference electrode
32 base layer
33 silver chloride layer
34 chloride layer
40 temperature probe
41 temperature sensor
50 electrical conductivity probe
51 electrical conductivity electrode pair
52 electrode
60 heater-equipped temperature probe
61 temperature sensor
62 heater

The invention claimed is:

1. A vascular sap measurement sensor comprising:
an indicator electrode probe that includes an indicator electrode which is an ion-sensitive field effect transistor;
a reference electrode probe that includes a solid reference electrode, the solid reference electrode including a base layer, a silver chloride layer, and a chloride layer, the base layer being formed of an electrically conductive body, the silver chloride layer being formed on a surface of the base layer, the chloride layer being formed on a surface of the silver chloride layer;
an electrical conductivity probe that includes an electrical conductivity electrode pair, the electrical conductivity electrode pair including a pair of electrodes disposed at a predetermined interval; and
a supporting portion that supports the indicator electrode probe, the reference electrode probe and the electrical conductivity probe arranged in parallel, wherein each of the pair of electrodes includes a metal layer that covers a top surface and side surfaces of a projection formed on a probe surface.

2. The vascular sap measurement sensor according to claim 1, comprising
a temperature probe that includes a temperature sensor, wherein the temperature probe is supported by the supporting portion.

3. The vascular sap measurement sensor according to claim 1, wherein the electrical conductivity electrode pair has a cell constant of 500 to 2,000 $m^{-1}$.

4. The vascular sap measurement sensor according to claim 1, wherein the pair of electrodes are arranged side by side along a width direction of the electrical conductivity probe.

5. The vascular sap measurement sensor according to claim 1, wherein the pair of electrodes are arranged side by side along an axial direction of the electrical conductivity probe.

6. The vascular sap measurement sensor according to claim 1, wherein the indicator electrode, the solid reference electrode, and the electrical conductivity electrode pair are disposed at a same position in a sticking direction to a plant.

7. The vascular sap measurement sensor according to claim 1, wherein
the indicator electrode and the solid reference electrode are disposed at positions different from the electrical conductivity electrode pair in a sticking direction to a plant, and
the electrical conductivity electrode pair is disposed in a xylem of the plant with the indicator electrode and the solid reference electrode disposed in a phloem of the plant.

8. The vascular sap measurement sensor according to claim 1, comprising:
a heater-equipped temperature probe that includes a temperature sensor and a heater; and
a temperature probe that includes a temperature sensor, wherein
the heater-equipped temperature probe and the temperature probe are supported by the supporting portion.

9. The vascular sap measurement sensor according to claim 8, further comprising
two of the temperature probes, wherein the two temperature probes are disposed at positions across the heater-equipped temperature probe.

10. A vascular sap measurement sensor, comprising:
an indicator electrode probe that includes an indicator electrode which is an ion-sensitive field effect transistor;
a reference electrode probe that includes a solid reference electrode, the solid reference electrode including a base layer, a silver chloride layer, and a chloride layer, the base layer being formed of an electrically conductive body, the silver chloride layer being formed on a surface of the base layer, the chloride layer being formed on a surface of the silver chloride layer; and
a supporting portion that supports the indicator electrode probe and the reference electrode probe arranged in parallel, wherein the chloride layer is produced by mixing and solidifying a glass paste and a potassium chloride at a weight ratio of 1:0.05 to 0.10.

* * * * *